(12) United States Patent
Wadsworth et al.

(10) Patent No.: US 6,632,670 B1
(45) Date of Patent: Oct. 14, 2003

(54) AAV VECTORS FOR GENE THERAPY

(75) Inventors: Samuel C. Wadsworth, Shrewsbury, MA (US); Karen Vincent, Arlington, MA (US); Susan Piraino, Framingham, MA (US); Sirkka Kyostio, Ashland, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 09/029,705

(22) PCT Filed: Sep. 6, 1996

(86) PCT No.: PCT/US96/14423

§ 371 (c)(1),
(2), (4) Date: Nov. 16, 1998

(87) PCT Pub. No.: WO97/09441

PCT Pub. Date: Mar. 13, 1997

Related U.S. Application Data

(60) Provisional application No. 60/003,470, filed on Aug. 9, 1995.

(51) Int. Cl.$^7$ .................. C12N 15/864; C12N 15/861; C12N 15/63; C12N 15/64

(52) U.S. Cl. ................ 435/455; 435/235.1; 435/320.1; 435/456; 435/457

(58) Field of Search .......................... 435/235.1, 320.1, 435/455, 456, 457

(56) References Cited

U.S. PATENT DOCUMENTS

| | | | |
|---|---|---|---|
| 5,168,062 A | * | 12/1992 | Stinski |
| 5,436,146 A | * | 7/1995 | Shenk et al. |
| 5,872,005 A | * | 2/1999 | Wang et al. ............... 435/320.1 |
| 6,004,797 A | | 12/1999 | Colosi ..................... 435/235.1 |
| 6,040,183 A | * | 3/2000 | Ferrari et al. ............... 435/457 |

FOREIGN PATENT DOCUMENTS

| | | |
|---|---|---|
| EP | 592836 | 4/1994 |
| WO | WO 9514771 | 6/1995 |
| WO | WO 9615777 | 5/1996 |
| WO | WO 9618727 | 6/1996 |

OTHER PUBLICATIONS

Rolling et al. "AAV as a viral vector for human gene therapy", Molecular Biothechnology, vol. 3, 1995, pp 9–15.

Clark et al. "Cell Lines for the production of recombinant adeno–associated virus" Human Gene Therapy, vol. 6, Oct. 1995, pp. 1329–1341.

Weitzman et al. "Adeno–associated virus (AAV) rep proteins mediate complex–formation between AAV DNA and its integration site in human DNA", Proceedings of the National Academy of Sciences, vol. 91, No. 13, 1994, pp. 5808–5812.

Walsh et al., "Regulated high–level expression of a human gamma–globin gene introduced into erythroid cells by an adeno–associated vector", Proceedings of the National Academy of Sciences, vol. 89, No. 15, Aug. 1992, pp. 7257–7261.

Flotte et al., "An improved system for packaging recombinant adeno–associated virus vectors capable of in vivo transduction", Gene Therapy, vol. 2, Jan. 1995, pp. 29–37.

Zhou et al. "Adeno–associated virus 2–mediated transduction and erythroid cell–specific expression of a human beta–globin gene" Gene Therapy, vol. 3, Mar. 1996, pp. 223–229.

Kotin et al. "Characterization of a preferred site of human chromosome 19q for integration of adeno–associated virus DNA by non–homologous recombination", vol. 11, No. 13, 1992, pp. 5071–5078.

\* cited by examiner

Primary Examiner—David Guzo

(57) ABSTRACT

The present invention is directed to methods for generating high titer, contaminant free, recombinant AAV vectors, methods and genetic constructs for producing recombinant AAV vectors conveniently and in large quantities, methods for the delivery of all essential viral proteins required in trans for high yields of recombinant AAV, recombinant AAV vectors for use in gene therapy, novel packaging cell lines which obviate the need for cotransfection of vector and helper plasmids, helper plasmids and vector plasmid backbone constructs, a reporter assay for determining AAV vector yield. Further provided are recombinant AAV vectors in a pharmaceutically acceptable carrier, methods of delivering a transgene of interest to a cell, compositions and methods for delivering a DNA sequence encoding a desired polypeptide to a cell, and transgenic non-human mammals that express a human chromosome 19 AAV integration locus.

17 Claims, 13 Drawing Sheets

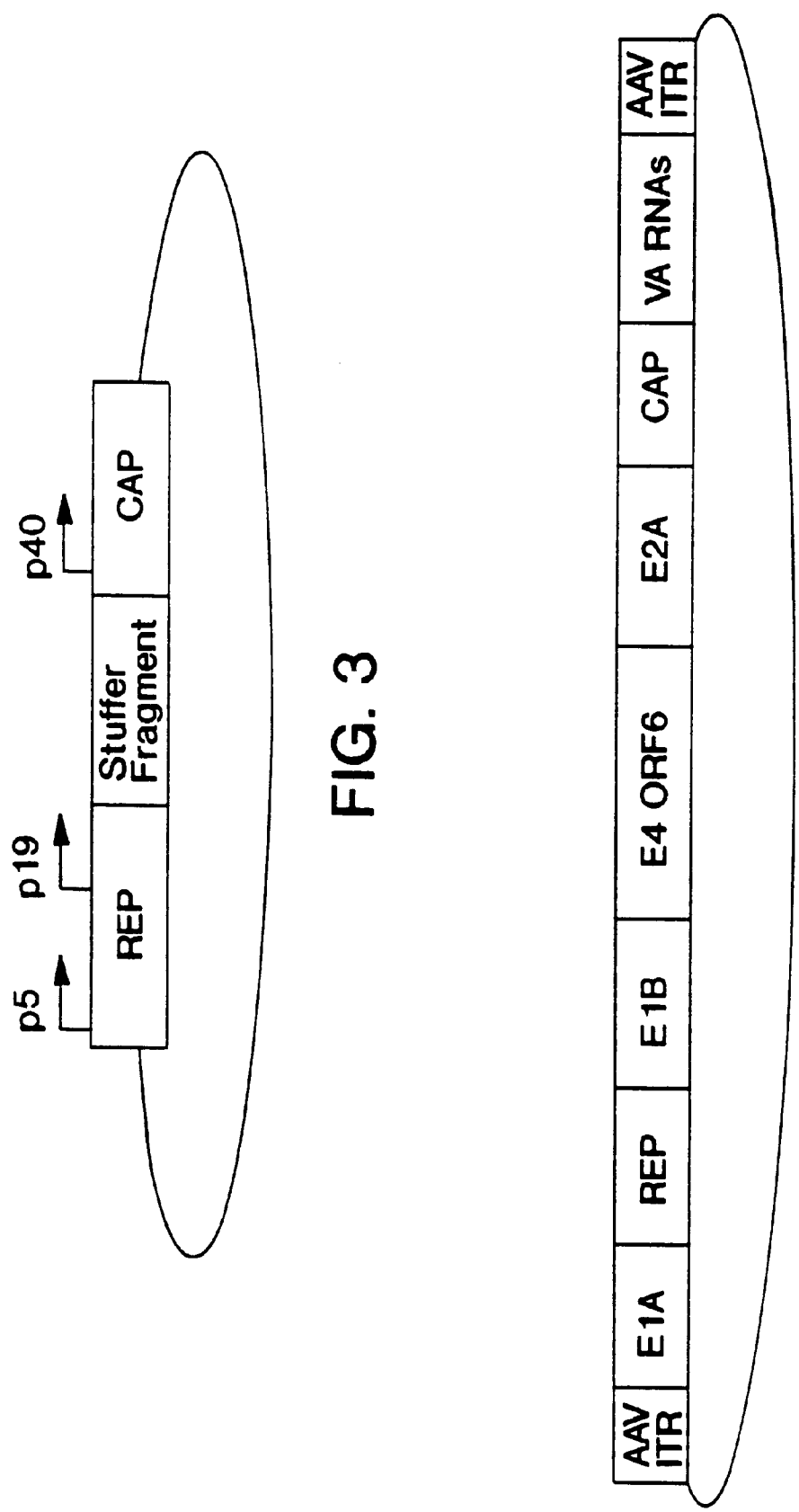

SEQUENCE LISTING

<160> NUMBER OF SEQ ID NOS: 8

<210> SEQ ID NO 1
<211> LENGTH: 27
<212> TYPE: DNA

```
<213> ORGANISM: Oligonucleotide primer

<400> SEQUENCE: 1
ggattacctc ggagaagcag tggatcc                                          27

<210> SEQ ID NO 2
<211> LENGTH: 29
<212> TYPE: DNA
<213> ORGANISM: Oligonucleotide primer

<400> SEQUENCE: 2
gtttgggttc actgatgtct gcgtcactg                                        29

<210> SEQ ID NO 3
<211> LENGTH: 10
<212> TYPE: DNA
<213> ORGANISM: Oligonucleotide-region of p40 TATA box

<400> SEQUENCE: 3
tataagtgag                                                             10

<210> SEQ ID NO 4
<211> LENGTH: 10
<212> TYPE: DNA
<213> ORGANISM: Oligonucleotide-mutation in p40 TATA bo

<400> SEQUENCE: 4
catcagtgaa                                                             10

<210> SEQ ID NO 5
<211> LENGTH: 39
<212> TYPE: DNA
<213> ORGANISM: Oligonucleotide primer

<400> SEQUENCE: 5
gtgtggaatc tttgcccaga tgggcccggt ttgagcttc                             39

<210> SEQ ID NO 6
<211> LENGTH: 30
<212> TYPE: DNA
<213> ORGANISM: Oligonucleotide primer

<400> SEQUENCE: 6
cagtgacgca gacatcagtg aacccaaacg                                       30

<210> SEQ ID NO 7
<211> LENGTH: 50
<212> TYPE: DNA
<213> ORGANISM: Oligonucleotide probe

<400> SEQUENCE: 7
actgctgcca ggcgctgatg tgcccggctt ctgaccatgc ggtcgcgttc                 50

<210> SEQ ID NO 8
<211> LENGTH: 50
<212> TYPE: DNA
<213> ORGANISM: Unknown Organism
<220> FEATURE:
<223> OTHER INFORMATION: Description of Unknown Organism:  to be filled

<400> SEQUENCE: 8
tcggaggaag caaggtgcgc gtggaccaga aatgcaagtc ctcggcccag                 50
```

AAV VECTORS FOR GENE THERAPY

This application is a 371 application of PCT/US96/14423, filed Sep. 6, 1996, which claims priority to provisional application No. 60/003,470 filed Sep. 8, 1995.

BACKGROUND OF THE INVENTION

Adeno-associated virus (AAV) is a parvovirus having a single-stranded DNA genome of about 4.6 kb. Unlike other viruses, AAV is naturally defective, requiring coinfection with a helper virus (e.g. adenovirus or herpes virus) to establish a productive infection. No human disease has been found to be associated with AAV infection (Blacklow et al., 1968). The host range of AAV is broad; unlike retroviruses, AAV can infect both quiescent and dividing cells in vitro and in vivo (Flotte et al., 1993; Kaplitt et al., 1994; Podsakoff et al., 1994; Russell et al., 1994) as well as cells originating from different species and tissue types in vitro (Lebkowski et al., 1988; McLaughlin et al., 1988). When infection occurs in the absence of a helper virus, wild-type AAV can integrate into the cellular genome as a provirus, until it is rescued by superinfection with adenovirus. (Handa et al., 1977; Cheung et al., 1980; Laughlin et al., 1986).

The AAV genome is relatively simple, containing two open reading frames (ORFs) flanked by short inverted terminal repeats (ITRs). The ITRs contain, inter alia, cis-acting sequences required for virus replication, rescue, packaging and integration. The integration function of the ITR permits the AAV genome to integrate into a cellular chromosome after infection.

The nonstructural or replication (Rep) and the capsid (Cap) proteins are encoded by the 5' and 3' ORFs, respectively. Four related proteins are expressed from the rep gene; Rep78 and Rep68 are transcribed from the p5 promoter while a downstream promoter, p19, directs the expression of Rep52 and Rep40. The larger Rep proteins (Rep78/68) are directly involved in AAV replication as well as regulation of viral gene expression (for review, see Muzyczka, 1992). The cap gene is transcribed from a third viral promoter, p40. The capsid is composed of three proteins of overlapping sequence; the smallest (VP-3) is the most abundant. Because the inverted terminal repeats are the only AAV sequences required in cis for replication, packaging, and integration (Samulski et al., 1989), most AAV vectors dispense with the viral genes encoding the Rep and Cap proteins and contain only the foreign gene inserted between the terminal repeats.

Interest in AAV as a vector in gene therapy results from several unique features of its biology. Stable genetic transformation, ideal for many of the goals of gene therapy, may be achieved by use of such AAV vectors. Furthermore, the site of integration for AAV is well-established as being on chromosome 19 of humans. This predictability removes the danger of random insertional events into the cellular genome that may activate or inactivate host genes or interrupt coding sequences, consequences that limit the use of vectors whose integration is random, e.g., retroviruses. Because the rep protein mediates the integration of AAV, it is believed that removal of this protein in the construction of AAV vectors result in altered integration patterns. In addition, AAV has not been associated with human disease, obviating many of the concerns that have been raised with virus-derived gene therapy vectors.

Notwithstanding the attractive aspects of AAV-based vectors, rapid progress in their evaluation for gene therapy has been hampered by the inability to produce recombinant viral stocks at large-scale and to high titer. The conventional method for production of recombinant AAV (rAAV) vectors is cotransfection of one plasmid containing the vector and a second helper plasmid encoding the AAV Rep and Cap proteins into 293 cells infected with adenovirus (e.g. Lebkowski et al., 1988; Samulski et al., 1989, Muzyczka, N., 1992, Kaplitt et al., 1994; Einerhand et al., 1995). This method is cumbersome and results in a low yield of rAAV, typically $10^4$–$10^5$ infectious or transducing units/ml. Strategies to improve this scheme have included increasing transfection efficiency by complexing plasmid DNA to adenoviral particles via polylysine (Mamounas et al., 1995), delivering the vector sequences as part of a recombinant adenovirus (Thrasher et al., 1995) and amplification of helper plasmid copy number by linkage to a SV40 replicon (Chiorini et al. 1995).

Progress in the development of AAV as a gene therapy vector has been limited by an inability to produce high titer recombinant AAV stock using the approaches described above. The limitations to date have been thought to derive from inadequate production of the AAV proteins required in trans for replication and packaging of the recombinant AAV genome. Trans-based strategies to vector production are those that modulate the level of proteins required in trans to effectuate AAV vector production. Attempts to increase the levels of these proteins have included placing the AAV rep gene under the control of the HIV LTR promoter (Flotte, F. R. et al., *Gene Therapy* 2:29–37, 1995) to increase protein levels and the development of cell lines that express the rep proteins (Yang, Q. et al., *J. Virol.* 68: 4847–4856, 1994).

The limitations in producing high titer AAV vector stock may also result from a failure to include AAV cis-required elements in the recombinant AAV vector design. Cis-based strategies to increase vector production are those that provide DNA sequences required in cis (in tandem) with the recombinant DNA to be packaged into the AAV vector particle. The trans and cis functions are related. Trans-required proteins are necessary to effectuate vector production, but they require cis-acting sequences in the recombinant AAV genome in order to be functionally active. Therefore, high yield AAV vector production requires a coordinated strategy of trans-based and cis-based improvements so that progress in the development of AAV as a standard gene therapy vehicle may be realized.

Thus, there is a need in the art for methods and compositions which enable production of high titer recombinant AAV (rAAV) preparations that are free from wild-type AAV and Adenovirus helper contamination.

SUMMARY OF THE INVENTION

The present invention is directed to methods for generating high titer, contaminant free, recombinant AAV vectors.

The present invention provides methods and genetic constructs for producing AAV recombinant vectors conveniently and in large quantities.

The present invention further provides methods for the delivery of all essential viral proteins required in trans for high yields of recombinant AAV.

The present invention provides recombinant AAV vectors for use in gene therapy, using trans- and cis-based strategies.

The present invention also provides novel packaging cell lines which obviate the need for cotransfection of vector and helper plasmids.

The invention is also directed to helper plasmids and vector plasmid backbone constructs that are used in these methods.

The present invention-provides a reporter assay for determining AAV vector yield.

Further provided are recombinant AAV vectors in a pharmaceutically acceptable carrier.

The present invention also provides methods of delivering a transgene of interest to a cell.

Compositions and methods for delivering a DNA sequence encoding a desired protein to a cell are provided by the present invention.

Still further provided are transgenic non-human mammals that express a human chromosome 19 AAV integration locus.

DESCRIPTION OF THE FIGURES

FIG. 3 shows a diagram of a nonreplicating helper plasmid containing the AAV rep and cap genes required for AAV vector production.

FIG. 4 shows a diagram of a replicating helper plasmid containing the adenovirus genes and AAV rep and cap genes required for AAV vector production.

DETAILED DESCRIPTION OF THE INVENTION

Figure 1:
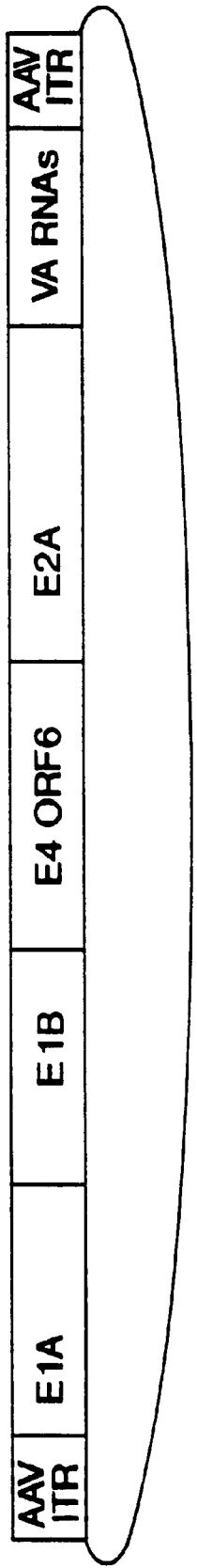
FIG. 1 shows a diagram of a replicating helper plasmid containing adenovirus genes required for AAV vector production.

All patent applications, patents, and literature references cited in this specification are hereby incorporated by reference in their entirety. In case of conflict or inconsistency, the present description, including definitions, will control.

Definitions 293 cells—human embryonic kidney cell line harboring and expressing parts of the adenovirus genome including the adenoviral E1 region.

293-MT-DBP cells—human embryonic kidney cell line modified to express parts of the adenovirus genome which complement recombinant adenovirus vectors that are deleted for E1 and E2A. Deposited Aug. 28, 1996 with the American Type Culture Collection, 12301 Parklawn Drive, Rockville, Md., and assigned ATCC CRL-12181.

2C4 cells—human embryonic kidney cell line modified to express parts of the adenovirus genome which complement recombinant adenovirus vectors that are deleted for E1 and E4. Deposited Aug. 28, 1996 with the American Type Culture Collection, 12301 Parklawn Drive, Rockville, Md., and assigned ATCC CRL-12182.

3B1 cells—human embryonic kidney cell line modified to express parts of the adenovirus genome which complement recombinant adenovirus vectors that are deleted for E1 and E2A. Deposited Aug. 28, 1996 with the American Type Culture Collection, 12301 Parklawn Drive, Rockville, Md., and assigned ATCC CRL-12183.

Cfu—colony forming units. For retroviral and adeno-associated virus vectors carrying antibiotic resistance genes, the number of antibiotic-resistant cell colonies after infection. It is assumed that one colony arises from a single infected cell.

Expression plasmid—extrachromosomal genetic elements that can propagate autonomously in cells, constructed in such a way that the genes carried in the plasmid can be expressed in the cells.

In cis—from the same DNA molecule.

In trans—from a different DNA molecule.

Insertional mutagenesis—the introduction of a mutation into a target gene by the insertion of foreign DNA, such as viral DNA, into the host-cell genome. The development of a mutation in a cellular gene as the result of the introduction of foreign DNA into a cell.

ITR—inverted terminal repeat, a DNA sequence that is repeated at either end of the virus in an inverted form.

Promoter-transgene cassette—a combination of DNA sequences containing elements necessary for directing production of a gene product and the DNA sequence of the gene itself.

Transduction—the introduction of foreign DNA into cells of an organism (in vivo).

Transfection—the introduction of foreign DNA into cells in culture (in vitro). Genetic modification of eukaryotic cells by introduction of foreign DNA using chemical means. In transient transfection, expression occurs from unintegrated foreign DNA and can be detected for a few days after transfection.

Transgene—a gene that has been stably incorporated into another organism.

Quiescent cells—cells that are not actively dividing.

Recombination—physical interaction between two or more DNA molecules, in this case viral sequences, leading to exchange of DNA sequence between the molecules.

Titer—the number of virus particles produced per ml. The assay system to determine the number of virus particles produced varies considerably depending on the virus in question. High titers are generally essential for successful gene therapy since they allow introduction of the therapeutic gene carried by the virus into the maximum number of cells.

Vector—a vehicle, usually a biological entity, such as a virus, used for the delivery of genes into an organism. A reagent that facilitates the introduction of foreign genes into cells.

LacZ gene—bacterial gene used as a cellular gene marker. Its expression is detected by a blue coloration in the presence of the substrate X-gal.

Packaging cells—cells that have been transfected with plasmids containing the cap and rep genes from AAV.

A purpose of the investigation described herein was to determine the limiting component(s) required for rAAV packaging. An understanding of the process at a basic level should benefit all methods of rAAV production. By selectively increasing expression of either the rep or cap genes (or both), it is shown that Cap protein production is one limiting factor in the production of rAAV.

A. Provision of Trans Product

1. Adenovirus Proteins

As discussed, adenovirus proteins are required to generate a productive AAV infection. In the absence of helper adenovirus, AAV integrates into the cellular genome, remaining latent until the cell is infected with adenovirus.

Adenovirus genes required for helper function include, inter alia, E1A, E1B, E2A, E4ORF6, and VA RNA (Muzycka, N., *Curr. Top. Micro. Immunol.* 158: 97–129, 1992). Standard methods of generating recombinant AAV vectors have relied on adenovirus infection of the target cell in order to provide adequate levels of necessary helper proteins. To avoid the unwanted generation of wild-type adenovirus that may occur during AAV vector production, an adenovirus containing a deletion is used in a cell line that provides an essential adenovirus protein in trans. Alternatively, a temperature-sensitive adenovirus replication mutant may be used at a nonpermissive temperature.

In one embodiment of the present invention, a helper plasmid is provided which contains the essential adenovirus helper genes bounded by AAV ITR sequences that allow the plasmid to replicate. The helper plasmid may contain E1A, E1B, E2A, E4 ORF6, and VA RNA genes. Each of these genes may also have its own promoter, through which transcription can occur. Alternative promoters that may be used in the helper plasmid include, but are not limited to, CMV, RSV, MMTV, E1A, EF1a, actin, cytokeratin 14, cytokeratin 18, PGK as well as others known to those skilled in the art.

Providing the essential adenovirus genes on a replicating plasmid is an alternative to infecting a host cell with adenovirus. The AAV ITR sequences in the plasmid function as an origin of replication under the control of the AAV rep proteins to increase the plasmid copy number. Increased copy number leads to increased levels of the proteins encoded by the genes on the plasmid. Thus, the helper plasmid of the present invention provides the adenovirus proteins required for AAV vector production, while eliminating the possibility of adenovirus production. A further advantage is that the levels of the adenovirus proteins are not limited by the amount of input plasmid DNA, since replication of the plasmid will increase gene copy number above input levels.

In additional embodiments, the origin of replication may include, but is not limited to, the SV40 origin of replication, the Epstein-Barr (EBV) origin of replication, as well as others known to those skilled in the art. Where, for example, an origin of replication requires an activating protein—e.g., SV40 origin requiring T antigen, EBV origin requiring EBNA protein—the activating protein may be provided by stable transfection so as to create a cell line source, or by transient transfection with a plasmid containing the appropriate gene.

Standard recombinant DNA techniques may be employed to construct the helper plasmids of the present invention (see, e.g., *Current Protocols in Molecular Biology*, Ausubel., F. et al., eds, Wiley and Sons, New York 1995). Such methods include the utilization of compatible restriction sites at the borders of the adenovirus genes and the ITR sequences or DNA linker sequences which contain restriction sites, as well as other methods known to those skilled in the art. Reference for adenovirus DNA sequence information is given in Roberts, R. J., in *Adenovirus DNA: The Viral Genome and Its Expression*, Oberfler, W., ed., Matinus Nihoff Publishing, Boston, 1986). Plasmids routinely employed in molecular biology—e.g., pBR322 (New England Biolabs, Beverly, Mass.), pRep9 (Invitrogen, San Diego, Calif.) or pBS (Stratagene, La Jolla, Calif.)—may be used as the basis for the helper plasmid into which adenovirus genes and the AAV ITR may be inserted. The adenovirus genes may be placed into the helper plasmid in any positional order. A particular embodiment of such a replicating helper plasmid according to the invention is shown in FIG. 1.

The helper plasmid may be used in the generation of recombinant AAV when combined with a source of the AAV rep and cap proteins, as well as the recombinant AAV genome. Transfection of cells by the plasmid using techniques well known in the art will provide the adenovirus gene products necessary for initiation of AAV rep gene expression.

2. AAV Proteins

In order to generate recombinant AAV vector stocks, standard approaches provide the AAV rep and cap gene products on a plasmid that is used to cotransfect a target cell along with the AAV vector plasmid. The levels of rep and cap proteins produced as a result of transfection are relevant to maximizing AAV vector production. This is because the rep proteins activate transcription of the cap gene, leading to production of the AAV structural proteins that are involved in packaging the recombinant genome.

Attempts to increase the levels of these AAV proteins in order to enhance vector production have been problematic (Kotin, R. M., *Human Gene Therapy* 5:793–81, 1994). One of the problems appears to be the toxicity of the rep protein to the cell at high levels.

Figure 2:
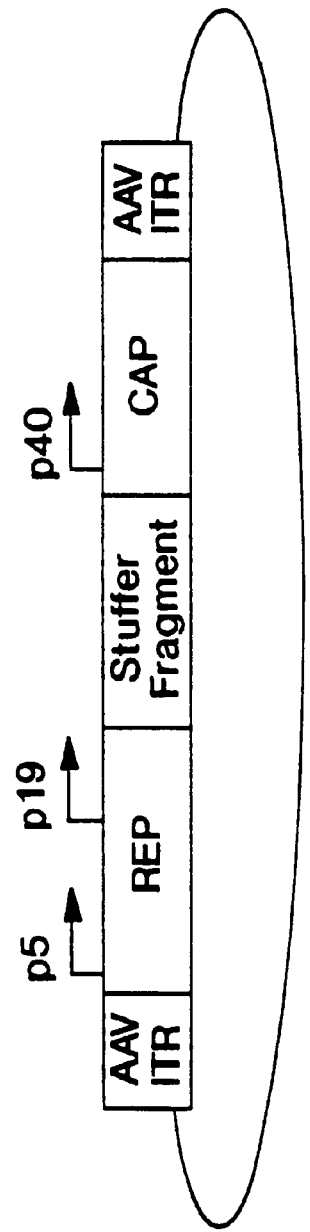
FIG. 2 shows a diagram of a replicating helper plasmid containing the AAV rep and cap genes required for AAV vector production.

In this aspect of the present invention, AAV rep and cap genes are provided on a replicating helper plasmid that contains the AAV ITR sequences. The rep proteins activate ITR as an origin of replication, leading to replication of the plasmid, that result in increased copy number. The advantage of this method is that rep protein level is not simply dependent on the efficiency of transfection with the plasmid, but is also a function of the replication of the plasmid following transfection. An example of a replicating helper plasmid containing the AAV rep and cap genes is provided in FIG. 2. In other embodiments of this aspect of the invention, the origin of replication may include, but is not limited to, the SV40 origin of replication, the Epstein-Barr (EBV) origin of replication, as well as others known to those skilled in the art. Where, for example, an origin of replication requires an activating protein—e.g., SV40 origin requiring T antigen, EBV origin requiring EBNA protein—the activating protein may be provided by stable transfection so as to create a cell line source, or by transient transfection with a plasmid containing the appropriate gene.

In still another embodiment of the invention, AAV rep and cap genes may be provided on a non-replicating plasmid, which does not contain an origin of replication. Such non-replicating plasmid further insures that the replication apparatus of the cell is directed to replicating recombinant AAV genomes, in order to optimize production of virus. Furthermore, since some studies have suggested that high levels of rep protein may be toxic to the cell (Muzyczka, N., *Curr. Top. Micro. Immunol.* 158: 97–129, 1992), providing the rep gene on a non-replicating plasmid may decrease this possibility. The levels of the AAV proteins encoding by such non-replicating plasmids may be modulated by use of particular promoters to drive the expression of these genes. Such promoters include, inter alia, AAV promoters, as well as promoters from exogenous sources, e.g., CMV, RSV, MMTV, E1A, EF1a, actin, cytokeratin 14, cytokeratin 18, PGK, as well as others known to those skilled in the art. An example of a non-replicating AAV helper plasmid is provided in FIG. 3.

Levels of rep and cap proteins produced by these helper plasmids may be individually regulated by the choice of a promoter for each gene that is optimally suited to the level of protein desired. Specific modulation of a particular gene—e.g., the rep gene—may also be achieved with the use of an inducible promoter. Such inducible promoters include, but are not limited to, MMTV, metallothionein, as well as others known to those skilled in the art.

In order to prevent any packaging of AAV genomic sequences containing the rep and cap genes, a plasmid containing the rep and cap DNA fragment may be modified by the inclusion of a "stuffer" fragment into the AAV genome which causes the DNA to exceed the length for optimal packaging. Thus, the helper fragment is not packaged into AAV virions. This is a safety feature, ensuring that only a recombinant AAV vector genome that does not exceed optimal packaging size is packaged into virions. An AAV helper fragment that incorporates a stuffer sequence exceeds the wild-type genome length of 4.6 kb, and lengths above 105% of the wild-type will not be packaged. The stuffer fragment may be derived from, for example, such non-viral sources as the β-galactosidase gene.

Standard recombinant DNA techniques may be employed to construct the helper plasmids of the present invention (see e.g., *Current Protocols in Molecular Biology*, Ausubel., F. et al., eds, Wiley and Sons, New York 1995), including the utilization of compatible restriction sites at the borders of the genes and AAV ITR sequences (where used) or DNA linker sequences which contain restriction sites, as well as other methods known to those skilled in the art. Reference for AAV DNA sequence information is given in Srivastava, A. et al., *J. Virol.* 45:555–564, 1983. Plasmids routinely employed in molecular biology may be used as a backbone—e.g., pBR322 (New England Biolabs, Beverly, Mass.), pRep9 (Invitrogen, San Diego, Calif.), pBS (Stratagene, La Jolla, Calif.)—for the insertion of the AAV genes and, in the case of a replicating plasmid, the AAV ITR.

3. Hybrid Helper Plasmid

Generation of a recombinant AAV vector stock requires both AAV and adenovirus proteins, provided in trans, in order to facilitate transcriptional activation, replication and packaging of the recombinant AAV genome. Standard approaches have utilized plasmid-based delivery of AAV genes into the target cell. Infection of the target cell with adenovirus is used to provide adenovirus genes. This multi-step protocol requires coordination of transfection and infection. Furthermore, infection of the cell with adenovirus allows for adenovirus production, which is not desirable when attempting to produce a pure AAV vector stock. In addition, the introduction of many viral genes which are not needed in vector generation causes diversion of transcriptional and replication machinery that could be directed to more efficient production of the essential proteins for AAV production. While AAV vectors have been produced using adenovirus genes introduced by infection, high yield vector production remains problematic. Therefore, a more efficient delivery of the genes coding for the proteins required in trans should improve AAV vector production.

The present invention provides a simple method for the delivery of all essential viral proteins required in trans for high yields of AAV. A hybrid plasmid is constructed to carry AAV and adenovirus genes encoding the essential proteins. The advantages of such a plasmid include, inter alia, a single entry event into the cell delivering all genes coding for trans-acting proteins, coordinate provision of all such genes and avoidance of adenovirus production resulting from the elimination of unnecessary adenovirus genes. Such a plasmid is shown in FIG. 4. The plasmid contains essential adenovirus genes—E1A, E1B, E2A, E4 ORF6, and VA RNA. The plasmid also contains the AAV rep and cap genes, as well as the AAV ITR sequences which are required to replicate the plasmid. The genes may be transcribed using their own promoters. Alternatively, promoters may include, but are not limited to, CMV, RSV, MMTV, E1A, EF1a, actin, cytokeratin 14, cytokeratin 18, PGK, as well as others known to those skilled in the art. The adenovirus genes may be inserted into the plasmid in the order shown in FIG. 4, or they may be inserted in any number of different positional arrangements that are within the ability of the skilled artisan to devise.

All essential genes required in trans may also be provided on two plasmids for ease of cloning. Thus, the AAV and adenovirus genes on the hybrid helper plasmid may be carried by two plasmids, in any optimal arrangement for cloning. In other words, the AAV and adenovirus genes do not have to be on separate plasmids.

Standard recombinant DNA techniques may be employed to construct the helper plasmids of the present invention (see, e.g., *Current Protocols in Molecular Biology*, Ausubel., F. et al., eds, Wiley and Sons, New York 1995), including the utilization of compatible restriction sites at the borders of the genes and the ITR sequences or DNA linker sequences which contain restriction sites, as well as other methods known to those skilled in the art. Reference for adenovirus and AAV DNA sequence information is cited above. Routinely used plasmids—e.g., pBR322 (New England Biolabs, Beverly, Mass.), pRep9 (Invitrogen, San Diego, Calif.), pBS (Stratagene, La Jolla, Calif.)—may be used for the insertion of the adenovirus and AAV genes and the AAV ITR. The adenovirus genes may be placed into the helper plasmid in any positional order.

4. Production of Recombinant AAV Vectors

Helper plasmids that provide essential proteins required in trans are used to generate recombinant AAV vector stock. These plasmids are introduced into the target cell using any number of transfection methods, including, inter alia, calcium-phosphate transfection, lipofection or other techniques known to those skilled in the art. The ratio of helper plasmids to the quantity of vector plasmid containing the gene of interest range from 1:1–1:10. This procedure produces recombinant AAV vectors; the vector plasmid contains the recombinant AAV genome flanked by the AAV ITRs.

Recombinant AAV vectors are produced using 293 cells in 8 roller bottles ($1 \times 10^9$ cells/ml). Cells are transfected with both the helper plasmid and the AAV vector plasmid at a vector:helper ratio of 1:10. The plasmids may be introduced into the target cell using any number of transfection methods, including, but not limited to, calcium-phosphate, lipofection, or other techniques known to those skilled in the art (see e.g., *Current Protocols in Molecular Biology*, Ausubel, F. et al., eds., Wiley and Sons, New York, 1995). In a preferred embodiment, lipofection is used for transfection. Adenovirus infection is initiated at a multiplicity of infection (MOI) of 20. The adenovirus strain may be a deletion virus, in which case, complementing genes are integrated into the cell line, or a temperature-sensitive mutant (e.g., ts149) which cannot replicate at a nonpermissive temperature (39° C.). The transfected/infected cells are then incubated for 2 days at the appropriate temperature. After incubation, the cells are harvested and then lysed by three (3) freezing and thawing cycles in the presence of benzonase (American International Chemical, Natick, Mass.). 1% deoxycholate and 0.25% trypsin is then added to the lysate, followed by incubation for 30 minutes at 37° C. The cell lysate (2 roller bottles/gradient) may then be applied to a CsCl step gradient (1.5 g/ml–1.36 g/ml) in a SW28 rotor and centrifuged at 26K for 6 hours at 4° C. Fractions are obtained and then further purified on two equilibrium gradients, using a NVT65 rotor, and centrifuged at 60K for 20 hours at 4° C. Fractions from the equilibrium gradients are screened on a refractometer and pooled. Pooled fractions are dialyzed in PBS with 1% sucrose 3 times for 2 hours at 4° C.

5. Assay for Recombinant AAV Vector Production

The efficiency of a helper plasmid as a source of proteins required in trans is determined from the yield of AAV vector stock. To determine virus yield, an AAV infectious center assay is used to assay for production of infectious progeny. The recombinant AAV vectors are recovered after production using the purification protocol described above. The assay shows whether infectious AAV progeny are produced in the production protocol.

The assay is performed with 293 cells that are plated on day one at a density of $1 \times 10^5$ cells per well in 0.1 ml/well in DME medium supplemented with 10% FBS, penicillin/streptomycin, and glutamine. After about 24 hours, the cells are infected with adenovirus at an MOI of 20 and with wild-type AAV at an MOI of 2. The viruses are suspended in the same medium, and 0.1 ml is added to each well to initiate infection. The AAV vector samples are added to the well (25–100 microliters of lysate or dilutions) and the plates are incubated for 24–30 hours at the appropriate temperature (37° C. for wild-type adenovirus; 39° C. for an adenovirus temperature-sensitive mutant). On the day after infection, the medium is carefully removed from the cells. Cold 0.2 ml PBS containing 5 mM EDTA is added to each well, and the plate is put on ice.

A filtration apparatus is then prepared for use by placing a nitrocellulose filter prewetted with PBS in position, and adding 5 ml of PBS to the top of the filtration unit. The cells in the plate are resuspended by pipetting. 0.05 ml of the cell suspension is added into the PBS buffer in the filtration unit and mixed by rotation. Suction is applied to the apparatus to deposit the cells onto the filters. The filters are air dried for 10 minutes. The cells are lysed on directly on the filters using denaturing solution followed by neutralizing solution. The filters are dried on paper for 5 minutes following each solution and then air dried for 10 minutes. The filters are washed in 2xSSC, air dried for 10 minutes, and baked in a vacuum oven for 2 hours. Hybridization to a probe that detects the gene of interest is performed using the filters prepared as above, wetted in 2xSSC. Filters can be prehybridized using 30–40 ml of Quick-Hyb® (Stratagene, La Jolla, Calif.) by incubating at 68° C. for 2–4 hours in a rotating water bath. The labelled probe is then added to the Quick-Hyb® solution, and incubated overnight at 68° C. Filters are washed the next day (5 minutes in 2xSSC, 0.5% SDS at room temperature, 15 minutes in 2xSSC 0.1% SDS at room temperature, followed by 2 hours in 0.1xSSC, 0.5% SDS at 65° C.). The filter is exposed to film overnight at −80° C. to produce an autoradiograph.

The number of infectious centers on the filter are counted on the autoradiograph. The titer of the starting material is determined by multiplying the number of infectious centers by any dilution used in the preparation of test samples.

Where the AAV vector in production contains a reporter gene, alternative methods for determining the AAV vector titer can be used. For example, if the lacZ gene is used, the infected cells can be stained for the expression of the gene product, β-galactosidase, using X-gal. Titer is determined, for example, by counting the blue-stained cells in a plate well.

B. AAV Vector Plasmid Constructs Containing Cis-Acting Sequences

The present invention also provides a means to increase the production of recombinant AAV vectors via AAV vector plasmid designs that utilize cis-acting sequences in the AAV genome required for efficient replication and packaging. The invention also provides vector plasmids designed to provide such cis-acting sequences.

Current vector plasmid designs place the gene of interest between the AAV ITR sequences to create a recombinant genome and provide no other AAV sequences. The AAV ITR sequences have cis-acting functions that facilitate replication and packaging of the recombinant genome during vector production, as well as integration of the vector DNA into a cell following its introduction by the AAV vector. Thus, ITR sequences are retained in recombinant AAV vector designs. However, the difficulty in achieving high titer production of AAV vectors indicates that the ITRs per se are not sufficient to provide all cis-acting functions necessary to the production-of high titer vector stock. Therefore, other cis-acting AAV sequences in addition to the ITRs are required within the vector construct in order to increase the efficiency of replication and/or packaging of the recombinant AAV genome.

Cis-acting elements in the AAV genome are believed to facilitate rescue and replication of the genome through interactions with the AAV rep proteins. It is known that rep proteins bind to sites in the AAV ITR as well as to sites in the AAV p5 and p19 promoters (McCarty, D. M. et al., *J. Virol.* 65: 2936–2945, 1991; McCarty, D. M. et al., *J. Virol.* 68:4988–4997, 1995). Cis-acting packaging elements also appear to be required in the recombinant AAV vector genome for maximal particle production.

The present invention provides a method to improve AAV vector production using vector backbone constructs that contain AAV sequences in addition to the ITR sequences. The AAV vector backbone may include AAV genomic fragments that contain rep-binding sites or critical packaging sequences. Because the precise number and location of all cis-acting AAV sequences has not yet been defined, construction of vector plasmids containing significant portions of the AAV genome is important to include all cis-acting sequences, including those that are still undefined. While these vector plasmid constructs improve the production of recombinant AAV vector stock, a further utility of the invention is that essential cis-acting sequences can be functionally identified through improved vector production.

The vector constructs containing such cis-acting sequences may be prepared using known techniques. (see e.g. *Current Protocols in Molecular Biology*, Ausubel., F. et al., eds, Wiley and Sons, New York 1995). The presence of known restriction sites in the AAV genome may be used to derive subgenomic fragments for insertion into a recombinant AAV vector. Fragment length is chosen so that the recombinant genome does not exceed the packaging capacity of the AAV particle. If necessary, a "stuffer" DNA sequence is added to the construct to maintain standard AAV genome size for comparative purposes. Such a fragment may be derived from such non-viral sources, e.g., lacZ, or other genes which are known and available to those skilled in the art.

Figure 5:
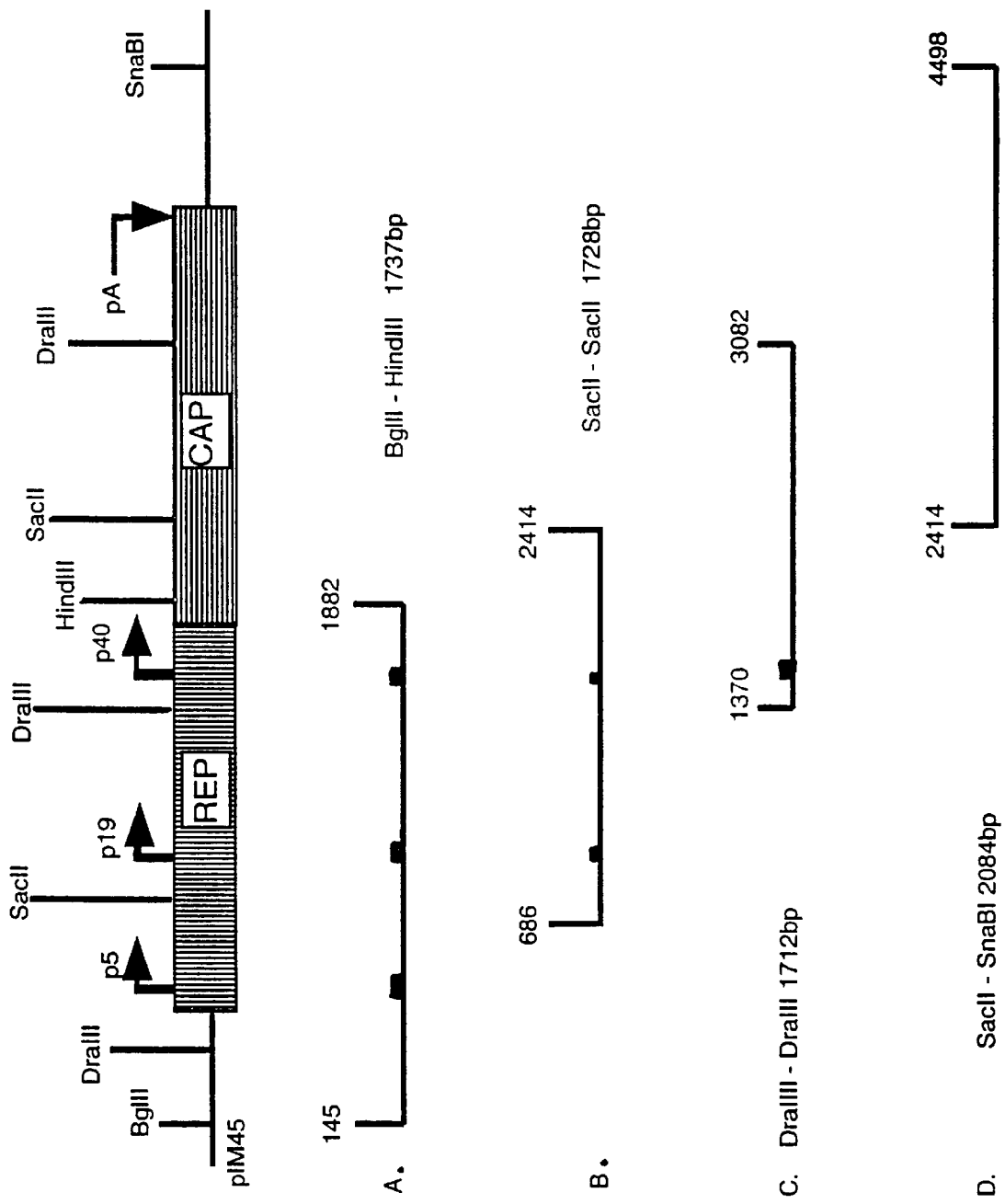
FIG. 5 shows a diagram of AAV subgenomic fragments to be used in vector plasmid constructs for AAV vector production. Reference is to restriction sites in pIM45 that define the borders of the fragments.

The present invention provides a series of vector plasmid constructs which add AAV subgenomic fragments into a vector plasmid containing a gene of interest flanked by the AAV ITRs. See FIG. 5. These fragments range in size from 1.7–2.1 kb. Because these fragments contain coding as well as noncoding regions of the AAV genome, effects on packaging may be due to elements acting in trans as well as in cis. Further modifications of the constructs shown—e.g., insertion of smaller AAV fragments—are within the scope of the invention, and may be readily made by those skilled in the art. When subgenomic fragments are used that are smaller than the coding regions in the genome, the effects observed on vector production are characterized as cis-acting effects. For example, standard deletion analysis approaches are suitable to refine subgenomic fragments to a minimal length needed for optimal vector production. Defined AAV cis-acting fragments—e.g., rep-responsive elements—are specifically cloned into the vector plasmids.

The present invention provides an efficient reporter assay for determining AAV vector yield for use in gene therapy. In this manner, the most efficient construct designs are identified by production of high titer stock.

Figure 6:
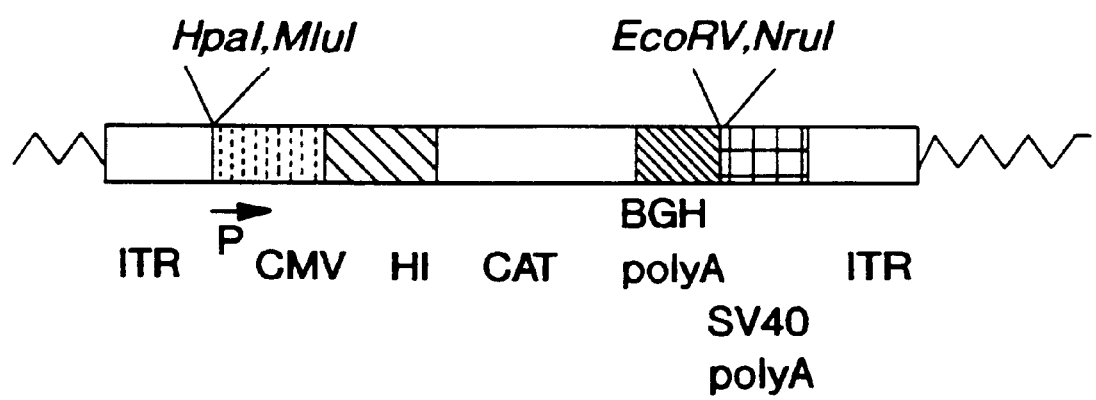
FIG. 6 shows a diagram of pTRCAT reporter plasmid.

A plasmid containing a reporter gene and the AAV ITR sequences is used to determine improvement in production efficiency when AAV sequences are added. This plasmid may be modified with the insertion of AAV subgenomic fragments to create additional constructs, such as plasmid pTR-CAT, shown in FIG. 6. This plasmid contains an expression cassette comprising the chloramphenicol acetyltransferase (CAT) gene under the control of CMV promoter, a hybrid intron and the BGH polyA site. The expression cassette was cloned into pUC-TR, a high copy number plasmid derived by cloning the AAV ITR region into pUC19. (New England Biolabs, Beverly, Mass.) The insertion of the expression cassette into pUC-TR created pTR-CAT. Restriction sites may be added at the 5' and 3' ends of the CAT cassette by inserting linkers or by using other techniques known to those skilled in the art. AAV subgenomic fragments may be inserted at these restriction sites. This reporter plasmid will accommodate the subgenomic fragments shown in FIG. 5 that may be placed at either the 5' or 3' end of the expression cassette. Optimally, it may be necessary to test the insertion of fragments at both ends in order to determine any positional effect that the placement of the insert might have. The fragment can also be inserted at both ends of the vector plasmid. One or more copies of a defined cis-acting element can increase the amount of vector produced.

The packaging of the novel constructs requires that of AAV rep and cap genes (e.g., using pIM45, described in EXAMPLE 1) be provided and as well as essential adenovirus genes. A plasmid containing the AAV genes is cotransfected with the novel construct. An adenovirus infection or an adenovirus helper plasmid of the present invention (See Section 1, supra) provides the other necessary genes.

An infectious center assay utilizing an appropriate probe is used for determining the amount of infectious progeny (see Section 5, supra). Alternatively, a reporter gene product in the AAV vector can be assayed directly—e.g., a CAT enzyme assay is used where this reporter gene is present, for example, pTR-CAT (*Current Protocols in Molecular Biology*, Ausubel, F. et al., eds., Wiley and Sons, New York, 1995).

Alternative reporter genes may be used in assaying the vector plasmid constructs provided that the final plasmid construct containing the reporter gene and the AAV cis-acting fragments do not exceed the packaging length for an AAV particle. Other reporter gene products may be detected in the infectious AAV particles using appropriate biochemical assay.

The invention provides transgenic non-human mammals capable of expressing the AAV integration locus on human chromosome 19. Examples of non-human transgenic mammals are transgenic cows, sheep, goats, pigs, rabbits, rats and mice.

Animal model systems which elucidate the physiological and behavioral roles of invention polypeptides are produced by creating transgenic animals in which the expression of a polypeptide of interest is altered or modified using a variety of techniques. Examples of such techniques include the insertion of normal or mutant versions of nucleic acids encoding a polypeptide of interest, by microinjection, retroviral infection or other means well known to those skilled in the art, into appropriate fertilized embryos to produce a transgenic animal. See, for example, Carver, et al., *Bio/Technology* 11:1263–1270, 1993; Carver et al., *Cytotechnology* 9:77–84, 1992; Clark et al, *Bio/Technology* 7:487–492, 1989; Simons et al., *Bio/Technology* 6:179–183, 1988; Swanson et al., *Bio/Technology* 10:557–559, 1992; Velander et al., *Proc. Natl. Acad. Sci. USA* 89:12003–12007, 1992; Hammer et al., *Nature* 315:680–683, 1985; Krimpenfort et al., *Bio/Technology* 9:844–847, 1991; Ebert et al., *Bio/Technology* 9:835–838, 1991; Simons et al., *Nature* 328:530–532, 1987; Pittius et al., *Proc. Natl. Acad. Sci. USA* 85:5874–5878, 1988; Greenberg et al., *Proc. Natl. Acad. Sci. USA* 88:8327–8331, 1991; Whitelaw et al., *Transg. Res.* 1:3–13, 1991; Gordon et al., *Bio/Technology* 5:1183–1187, 1987; Grosveld et al., *Cell* 51:975–985, 1987; Brinster et al., *Proc. Natl. Acad. Sci. USA* 88:478–482, 1991; Brinster et al., *Proc. Natl. Acad. Sci. USA* 85:836–840, 1988; Brinster et al., *Proc. Natl. Acad. Sci. USA* 82:4438–4442, 1985; A1-Shawi et al., *Mol. Cell. Biol.* 10(3):1192–1198, 1990; Van Der Putten et al., *Proc. Natl. Acad. Sci. USA* 82:6148–6152, 1985; Thompson et al., *Cell* 56:313–321, 1989; Gordon et al., *Science* 214:1244–1246, 1981; and Hogan et al., *Manipulating the Mouse Embryo: A Laboratory Manual* (Cold Spring Harbor Laboratory, 1986).

Another technique, homologous recombination of mutant or normal versions of these genes with the native gene locus in transgenic animals, may be used to alter the regulation of expression or the structure of the polypeptide of interest (see, Capecchi et al., *Science* 244:1288, 1989; Zimmer et al., *Nature* 338:150, 1989). Homologous recombination techniques are well known in the art. Homologous recombination replaces the native (endogenous) gene with a recombinant or mutated gene to produce an animal that cannot express native (endogenous) protein but can express, for example, a recombinant protein which results in expression, for example, of the human AAV integration locus.

In contrast to homologous recombination, microinjection adds genes to the host genome, without removing host genes. Microinjection can produce a transgenic animal that is capable of expressing both endogenous and exogenous polypeptides. Inducible promoters can be linked to the coding region of the nucleic acids to provide a means to regulate expression of the transgene. Tissue-specific regulatory elements can be linked to the coding region to permit tissue-specific expression of the transgene. Transgenic animal model systems are useful for in vivo screening of vector compositions for identification and confirmation of integration and long-term transgene expression.

C. Construction of AAV Helper Plasmids

Figure 11:
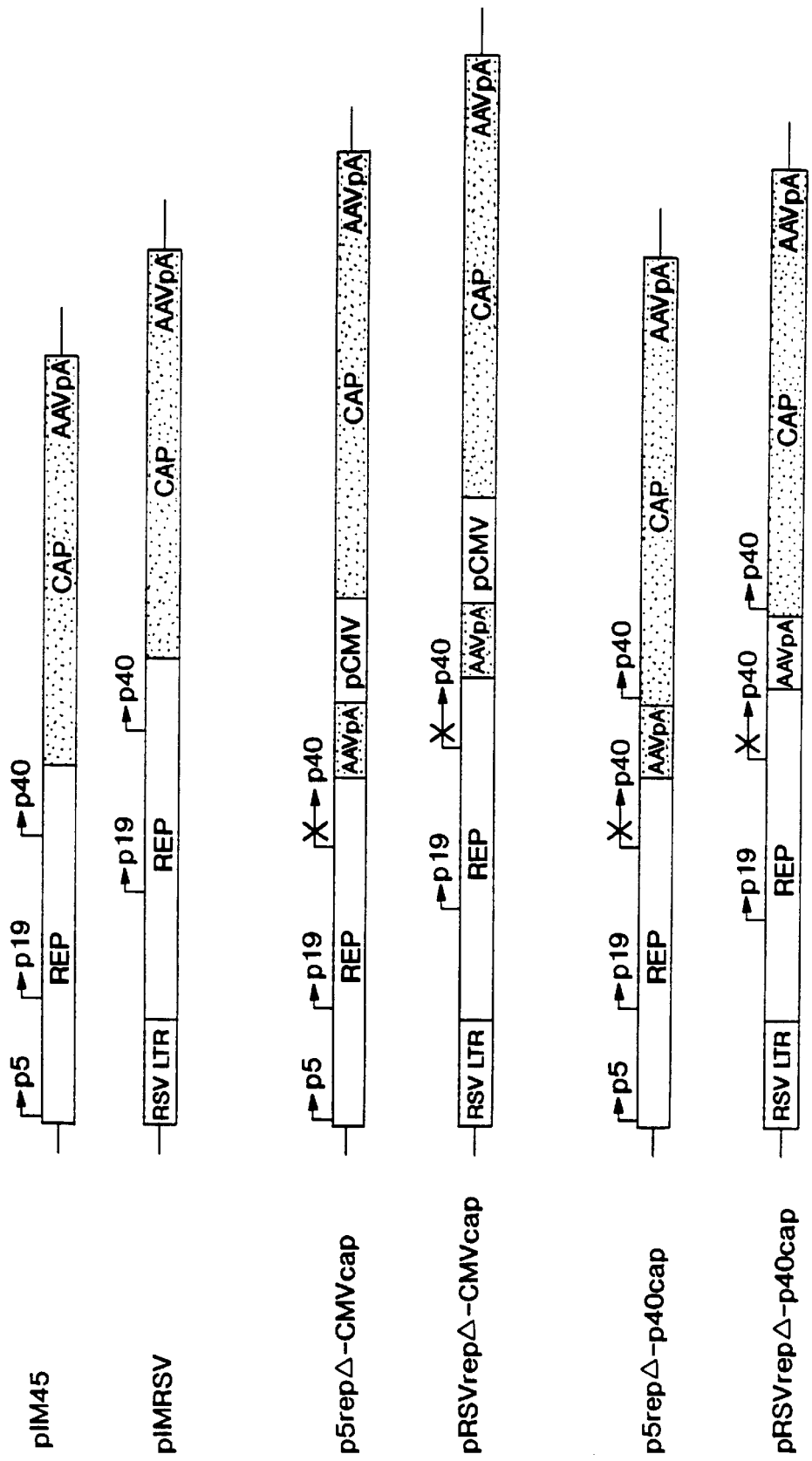
FIG. 11 shows AAV helper plasmids represented in linear form with the thin line (only a portion of which is shown) depicting the backbone plasmid DNA, the thick bars represent the Rep and Cap coding regions and their associated control regions, the arrows above the bars depict the positions of the endogenous AAV promoters, p5, p19 and p40, and the "X" indicates that the p40 promoter has been inactivated by mutation.

A series of helper plasmids was constructed to determine if rAAV packaging is limited by expression levels of the rep and/or cap genes (FIG. 11). Expression of Rep and Cap proteins was increased by replacing the endogenous AAV promoters, p5 and p40, with the RSV LTR and the CMV IE promoter, respectively. The starting helper plasmid, pIM45 (McCarty et al., 1991), contains a sequence encompassing the wild-type AAV genome but excluding the terminal repeats (nucleotides 145–4493). pIMRSV is a modification of pIM45 in which the RSV LTR replaces p5. Because p40 is located within the Rep coding region, the rep and cap genes were separated to allow replacement of p40 with the CMV IE promoter (as in p5repΔ-CMVcap). This strategy generated a vector with a direct repeat of 431 bp of sequence downstream from the p40 and CMV promoter. To prevent generation of wild type AAV through recombination, the p40 promoter lying within the rep ORF of this construct was inactivated by site-directed mutagenesis. p5repΔ-p40cap was constructed to express the rep and cap genes from endogenous AAV promoters as in pIM45, but so as to be more directly comparable to p5repΔ-CMVcap, the Rep and Cap coding regions were separated. RSVrepΔ-CMVcap and RSVrepΔ-p40cap are derivatives of p5repΔ-CMVcap and p5repΔ-p40cap, respectively in which p5 is replaced by the RSV LTR.

D. Rep and Cap Gene Expression from AAV Helper Plasmids

Figure 12B:
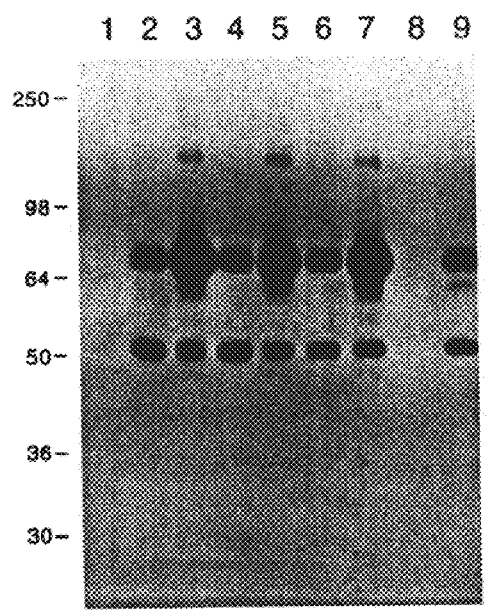
FIG. 12 shows Rep and Cap gene expression from AAV helper plasmids analyzed by Western blot using anti-Rep (panel A) and anti-Cap (panel B) primary antibodies. Lanes in each panel correspond to samples derived from cells transfected with the following helper DNAs: lane 1 (mock), lane 2 (pIM45), lane 3 (pIMRSV), lane 4 (p5repΔ-CMVcap), lane 5 (PRSV repΔ-CMVcap), lane 6 (p5repΔ-p40cap), lane 7 (pRSVrepΔ-p40cap), lane 8 (pIMRSV-am), lane 9 (wtAAV) MOI=10. Molecular weight size standards (in kD) are depicted to the left of each panel; each of the AAV Rep and Cap proteins is identified to the right.
Figure 12A:
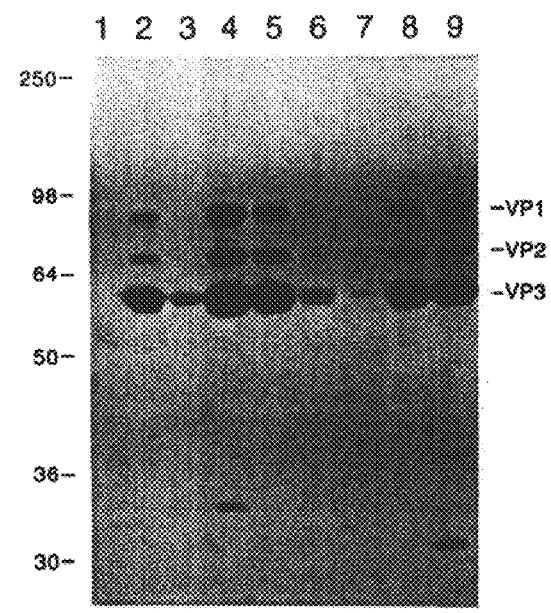

The amounts of Rep and Cap proteins expressed from each of the AAV helper plasmids were estimated by Western blot analysis (FIG. 12). The four Rep proteins produced following transfection into 293 cells in the presence of an Adts149 infection (MOI=20) comigrate with the corresponding proteins detected after coinfection of 293 cells with wild-type AAV (wtAAV) and Adts149. For each of the helper plasmids, Rep78 and Rep52 are the major proteins produced. Rep68 and Rep40, which are translated from spliced messages, were observed at a lower level. These were also detected as minor proteins in the wtAAV infection.

When the p5 promoter was replaced with the RSV LTR, an increase in the level of Rep78 was observed. This was the case for all three helpers, pIMRSV, RSVrepΔ-CMVcap and RSVrepΔ-p40cap. There was no change in the amount of Rep52, because in all constructs it was derived from a p19 transcript.

The three capsid proteins VP1, VP2, and VP3 were produced from all helper plasmids in the 1:1:10 ratio observed in a wt AAV infection (FIG. 12). Synthesis of all three capsid proteins was enhanced when p40 was replaced by the CMV IE promoter (FIG. 12 lane 2 vs. lane 4). However, expression of the rep gene from the RSV LTR appeared to have a down-regulatory effect on cap expression from p40. Thus, the level of capsid protein was reduced for pIMRSV relative to the parental plasmid containing p5 as the promoter regulating expression of rep (pIM45; compare lanes 3 and 2). A similar, but less dramatic effect was observed with capsid protein expression from the CMV IE promoter (lane 5 vs lane 4). In the latter case, a corresponding reduction was also seen in cap mRNA by Northern analysis, suggesting that overexpression of Rep78 results in transcriptional down-regulation of the CMV promoter. Cap protein synthesis was also reduced relative to pIM45 when the rep and cap genes were expressed from separate transcription units as in p5repΔ-p40cap where the AAVpA signal separates the rep and cap ORFs.

It should be noted that the total level of AAV proteins produced in the transient transfections was comparable to that observed in a wt AAV infection at an MOI of 10. While Rep78, Rep52 and the capsid proteins appeared at levels similar to that observed in the wt AAV infection when expressed from the AAV promoters (p5, p19 and p40, respectively), expression from the heterologous promoters, RSV LTR and the CMV IE, increased the amount above that observed in the viral infection. This is especially significant when it is considered that transfection efficiency ranges from 20–50% while infection at an MOI of 10 should occur with greater efficiency. This suggests that the concentration of each viral gene product per transfected cell is higher in the transient transfections than in the wt AAV infection.

E. Construction of PIM-RSVAM and Analysis of Cap Gene Down-Regulation

To analyze further the mechanism of down-regulation of capsid protein expression in the helper plasmids containing an RSV LTR-rep gene cassette, a derivative of pIMRSV was made that contained an amber mutation within the rep ORF (pIMRSV-am). If down-regulation were due to an alteration in cis (i.e. replacement of p5 with the RSV LTR), then it should persist in the amber mutant. In contrast, the down-regulatory effect should be relieved in the mutant if it is dependent upon synthesis of full-length Rep protein.

Figure 13A:
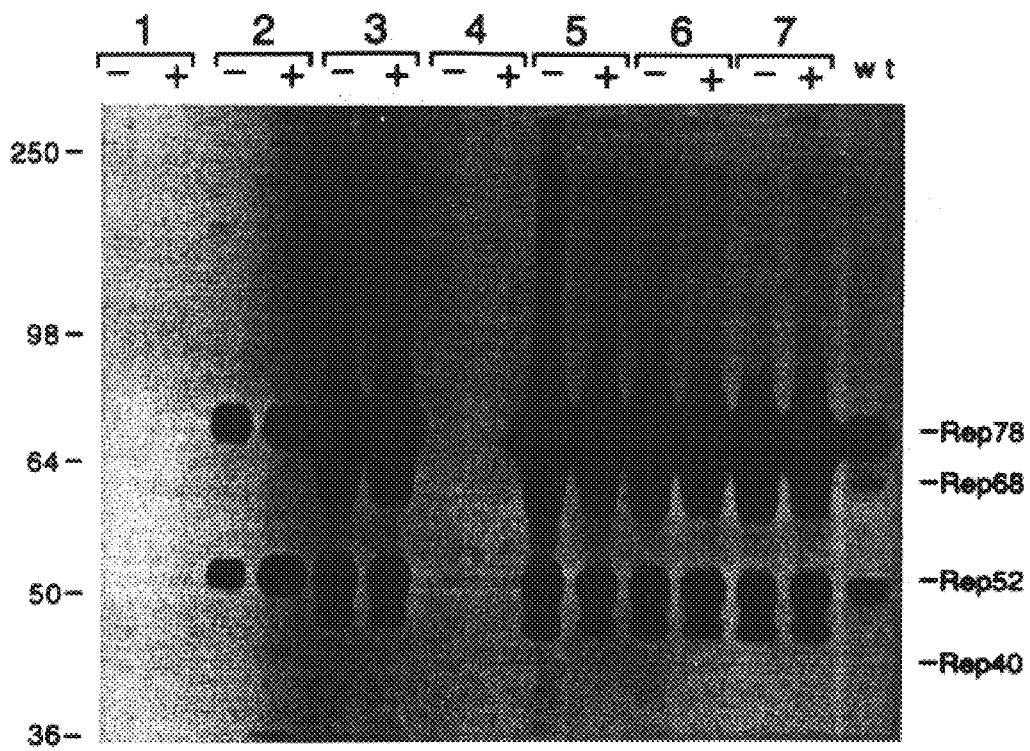
FIG. 13 is an analysis of the mechanism of down-regulation of the cap genes. Shown is a Western blot analysis of samples derived from 293 cells transfected with the appropriate DNAs (10 μg total) in the absence (−) or presence (+) of adenovirus (AD5ts149, MOI=20). Panel A and panel B show blots developed using an anti-Rep and anti-Cap primary antibodies, respectively. Lanes in each panel correspond to the following: lane 1 (mock transfected cells), lane 2, (pIM45), lane 3 (pIMRSV), lane 4 (pIMRSV-am), lane 5 (pIMRSV-am and suppressor tRNA plasmid), lane 6 (pIMRSV-am and pRSVRep), lane 7 (pRSVRep alone; "Wt"=cells infected with wtAAV (MOI=15) in the presence of adenovirus (Adts149, MOI=20). Molecular weight size markers (in kD) are shown at the left and the AAV Rep and Cap proteins are identified at the right.
Figure 13B:
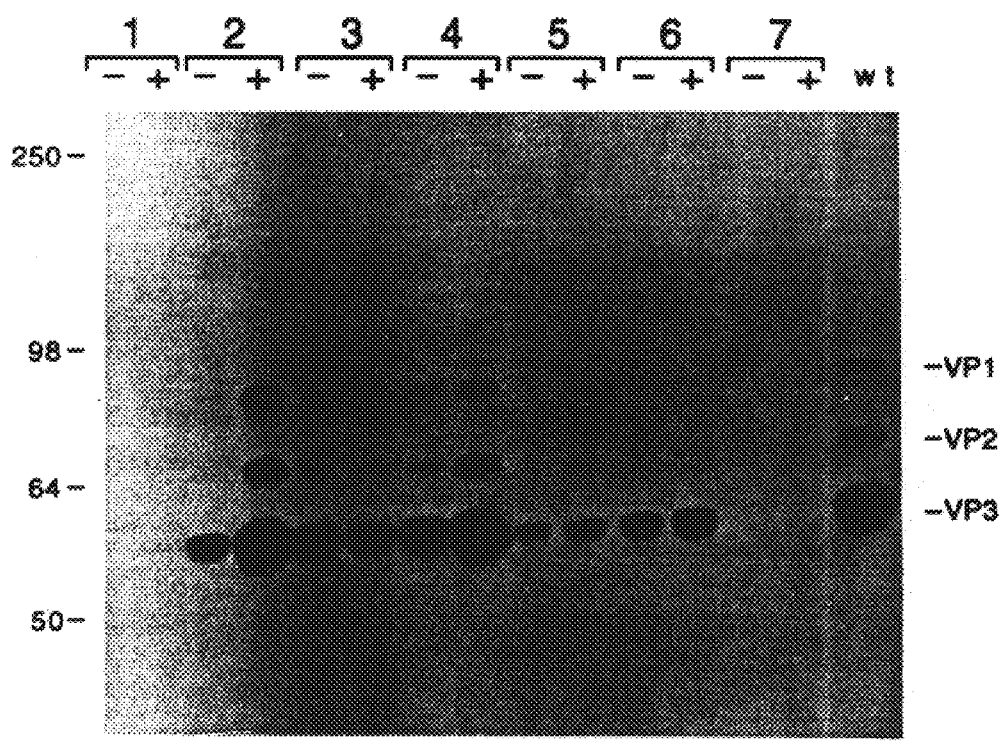

Transient transfections in 293 cells were performed using pIMRSV-am as a helper in the presence and absence of adenovirus (Ad) infection. Nuclear proteins were isolated and analyzed by Western blot (FIG. 13). With pIM45 as helper Rep78 appears at a high level in the absence of Ad due to expression of the E1A and E1B genes in 293 cells, hence the apparent lack of induction with the addition of Ad (induction of Rep78 with this construct is observed in HeLa cells). Infection with Ad does result in the appearance of the spliced Rep proteins, Rep68 and Rep40, and a slight increase in the level of Rep52. As expected, expression of Rep78 from the RSV promoter is unresponsive to Ad infection; the same high level appears in the presence and absence of helper virus coinfection. In cells transfected with pIMRSV-am, a small amount of full-length Rep78 is observed, indicating that the mutation is somewhat leaky. When cells are cotransfected with pIMRSV-am and an amber suppressor tRNA, production of Rep78 is restored to the level observed with pIMRSV. Cotransfection of pIMRSV-am with a Rep-expressing plasmid, pRSVrep, provides a high level of Rep78 in trans.

Capsid protein expression was analyzed in parallel (FIG. 13). Synthesis of the capsid proteins is significantly enhanced following Ad infection of cells transfected with pIM45. This increase is not observed with pIMRSV (lanes 5 and 6) but does occur with the pIMRSV-am mutant. The pIMRSV phenotype is restored when pIMRSV-am is cotransfected with the suppressor tRNA or when Rep protein is supplied in trans by cotransfection with pRSVrep.

Figure 14A:
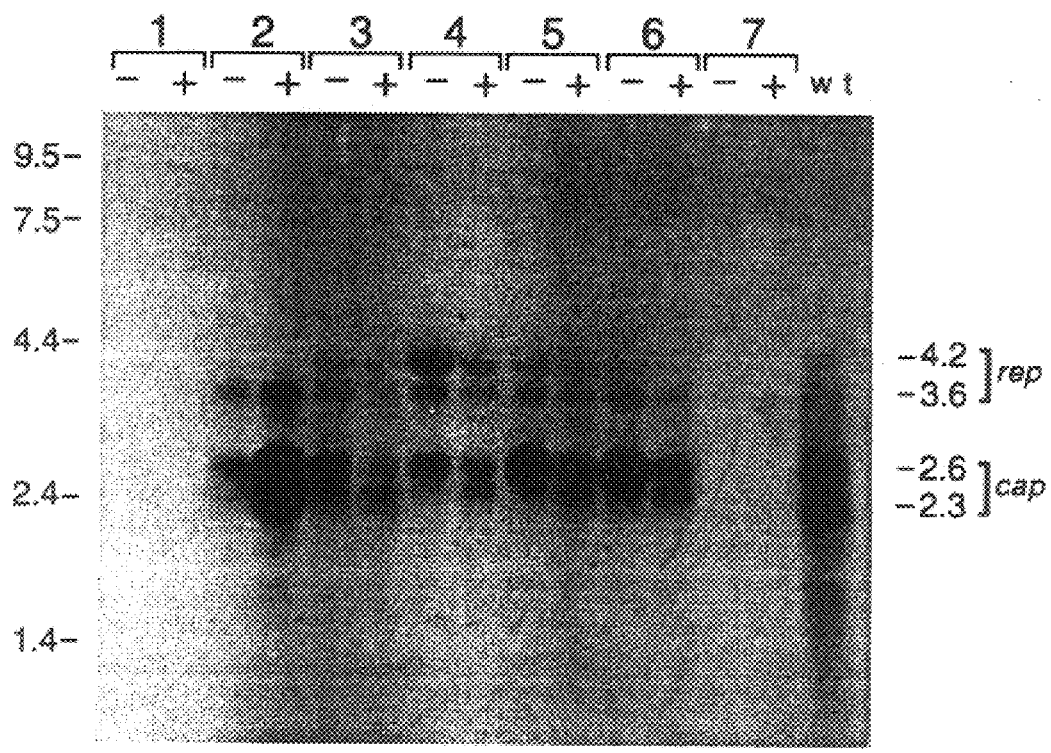
FIG. 14 is an analysis of total RNA derived from transfections described in FIG. 13. Panel A shows the Northern, panel B is the ethidium stained gel to demonstrate that equal amounts of RNA were loaded in each lane. Lanes in each panel correspond to the following: lane 1 (mock transfected cells), lane 2, (pIM45), lane 3 (pIMRSV), lane 4 (pIMRSV-am), lane 5 (pIMRSV-am and suppressor tRNA plasmid), lane 6 (pIMRSV-am and pRSVRep), lane 7 (pRSVRep alone; "Wt"=cells infected with wtAAV (MOI=15) in the presence of adenovirus (Adts149, MOI=20). Transfections were carried out in the absence (−) or presence (+) of adenovirus (AD5ts149, MOI=20). RNA size standards (in kilobases) are shown at the left in panel A, at the right in panel B; AAV mRNAs are identified at the right of panel A.
Figure 14B:
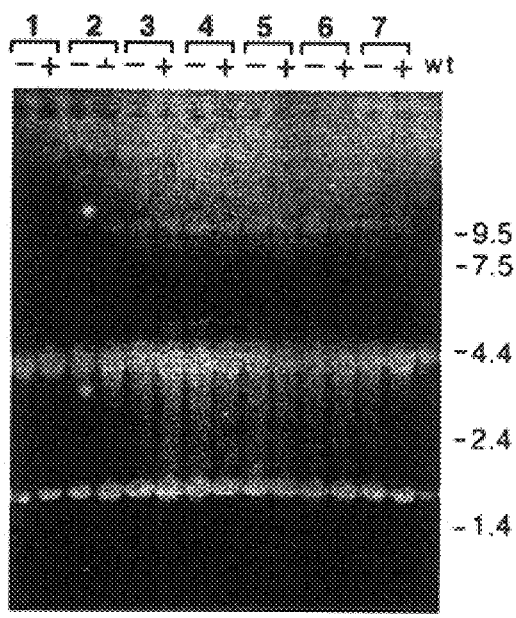
Figure 15A:
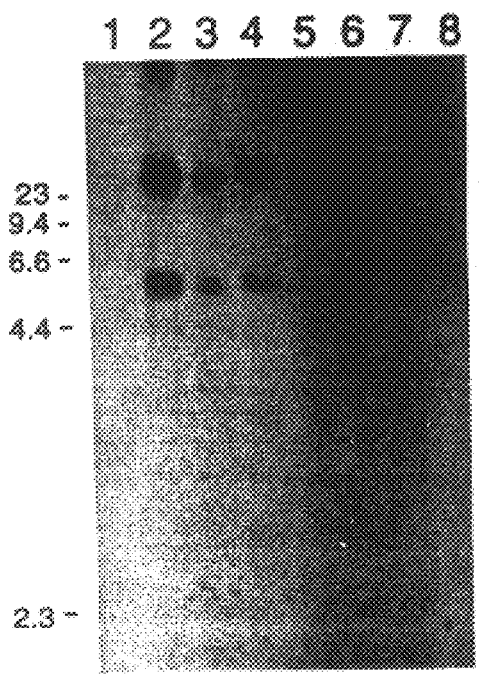
FIG. 15 is an analysis of vector replication and levels of wt AAV contamination. Adenovirus (Ad5ts149)—infected 293 cells were transfected with 1.5 μg of vector (pTRlacZ) and 15 μg of the indicated helper DNA. The replicated viral DNA was then analyzed by Southern blot; duplicate filters were probed with the lacZ probe. Panels C and D show primary and secondary Hirt DNAs, respectively, probed with the AAV fragment. For the primary DNAs (panels A and C), lanes correspond to the following samples: lane 1 (mock transfection), lane 2 (pIM45), lane 3 (pIMRSV), lane 4 (p5repΔ-CMVcap), lane 5 (RSVrepΔ-CMVcap), lane 6 (p5repΔ-p40cap), lane 7 (RSVrepΔ-p40cap), lane 8 (pIMRSV-am). For the secondary DNAs (panels B and D), the lanes are the same except the sample in lane 8 is derived from cells infected with wtAAV (MOI=0.001) and adenovirus (Ad5ts149, MOI=20). The positions of DNA size standards in (kilobase pairs) are depicted at the left of each panel; hybridizing bands corresponding to the dimer replicative form (dRF) and monomer replicative form (mRF) are identified at the right.
Figure 15B:
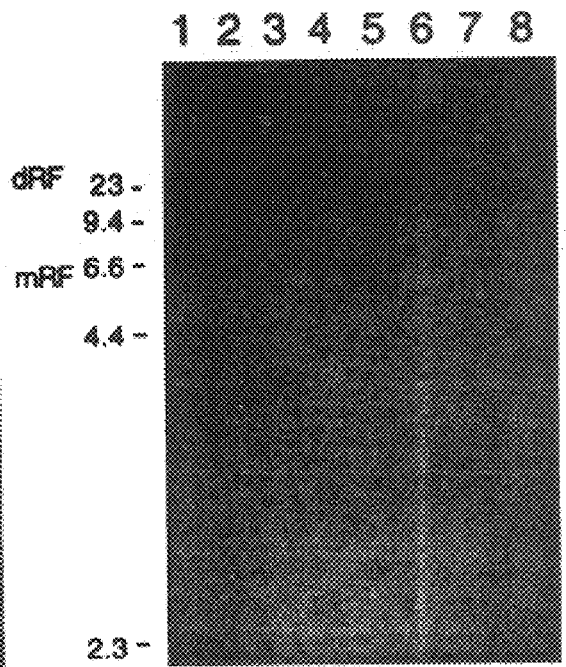
Figure 15C:
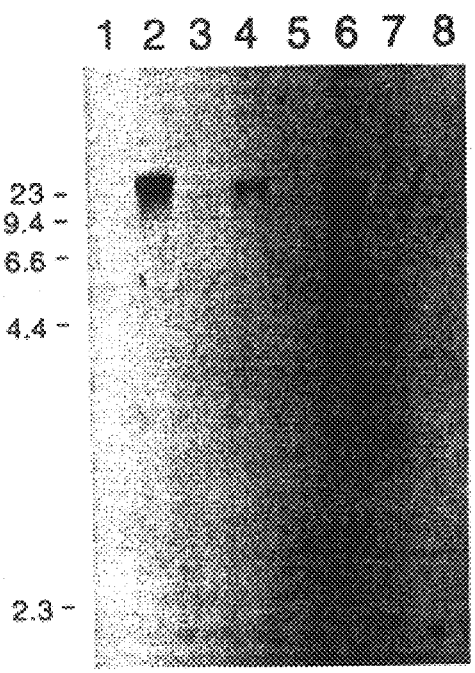
Figure 15D:
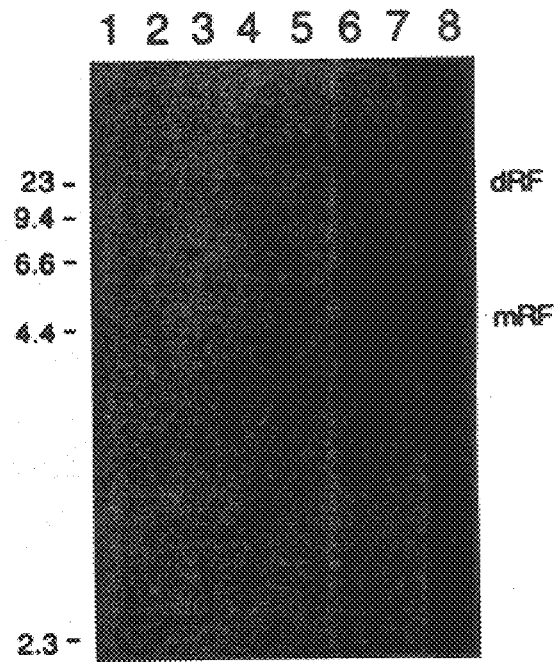

Northern analysis was performed on samples from the same experiment to examine this phenomenon at the RNA level (FIG. 14). With pIM45, a relatively low level of p5 transcript (4.2 kb) was observed, but the p19 transcript (3.6 kb) was more prevalent and showed an increase with Ad infection. The spliced transcripts from p5 and p19 (3.9 and 3.3 kb, respectively) were not-detected. Replacement of p5 by the RSV LTR resulted in an increase in the 4.2 kb transcript which contributes to the higher levels of Rep78 produced by this construct. Interestingly, the amount of this transcript was augmented further upon introduction of the amber mutation. When synthesis of Rep is restored by cotransfection of a suppressor tRNA (lane 5) or supplied in trans by cotransfection with pRSVrep (lane 6) synthesis of the 4.2 kb transcript is again reduced. These results suggest that transcription from the RSV LTR is down-regulated by Rep.

With pIM45, Ad infection results in a significant increase in both the full-length (2.6 kb) and spliced (2.3 kb) p40 mRNA, mirroring the increase in capsid protein synthesis. The prevalence of p40 transcripts over those derived from p5 and p19 is similar to that observed by Labow et al. (1986) from wt AAV in adenovirus-infected KB cells. In general, the ratios of. the two p40 mRNAs are shifted in favor of the spliced 2.3 kb transcript with Ad infection. In contrast to pIM45, no increase in the levels of either the p19 or p40 transcripts is observed with the pIMRSV construct upon Ad infection. Notably, with pIMRSV-am, the increase in capsid protein synthesis observed with Ad infection in the Western analysis (FIG. 13, lane 4) is not reflected by an increase in the level of cap mRNA. The level of capsid mRNA observed with pIMRSV-am is similar to that of the parental plasmid, pIMRSV. The same lower level is observed in the cotransfection of pIMRSV-am and the suppressor tRNA and of pIMRSV-am with the Rep-expressing plasmid, pRSVrep. The Northern analysis suggests that the reduced level of capsid protein synthesis observed with pIMRSV might-be explained at the RNA level by a failure to activate transcription from p40 in response to Ad infection. Furthermore, these results suggest that the increase in capsid protein production following Ad infection with the pIMRSV-am mutant is a post-transcriptional effect and that the mutation has relieved a Rep-mediated translational inhibitory effect on capsid synthesis.

F. rAAV Packaging: Comparison of RSVREP and CMV-CAP Helper Plasmids

The series of helper plasmids were compared with respect to their ability to produce rAAV. Each was transfected into Ad-infected 293 cells in conjunction with the pTRlacZ vector plasmid and the yield of rAAV in the crude lysate (Table 1) was determined by the titer assay. Increasing capsid protein expression by placing the cap gene under the control of the CMV promoter (p5repΔ-CMVcap) increased rAAV yield by approximately 9-fold. In contrast, replacing p5 with the RSV LTR in order to enhance rep gene expression resulted in a lower rAAV yield. When the RSV LTR was added to a construct containing p40 (pIMRSV or RSV repΔ-p40cap), rAAV titers were decreased by 10–20 fold, while the RSVrepΔ-CMVcap helper packaged rAAV 5-fold less efficiently than the comparable construct containing p5. These results correlate with differences in capsid protein expression observed in the Western analysis. As described above, a dramatic decrease in Cap protein production was observed as a result of overproduction of Rep 78 with the p40-cap constructs, while a more subtle effect was observed on Cap protein expression from the CMV promoter. The results of these experiments comparing the different helper constructs suggest that Cap, but probably not Rep protein synthesis is a limiting factor in the production of rAAV. The Tables provide the results of experiments showing the feasibility of producing recombinant AAV (rAAV) in the absence of adenovirus by providing the required adenovirus early genes (E1A and E1B, E4, E2A, VA) on plasmids.

Table 1: Shows a comparison of rAAV yield from the conventional production scheme (293 standard conditions) in the presence of adenovirus with that obtained in the absence of adenovirus. In the 'absence of adenovirus' cases, several different cell lines were used. Each cell line is a derivative of the 293 cell line (which contains the adenovirus E1 gene) that has been engineered to also contain the adenovirus E4 gene. The VK2-20 cell line was obtained from Frank Graham, while the other ORF 6 lines (2C4 and 3B1) were generated in-house. Since the VK2-20 and ORF6 lines already contain the E1A, E1B and E4 genes, in order to produce rAAV, the E2A and VA genes must be supplied by transfection with the E2VA plasmid. E2VA 5'→3' and E2VA 3'→5' are two clones of this plasmid (with the insert in opposite orientations). (The cells are also transfected with the rAAV vector plasmid and helper plasmid to allow production of rAAV). The conclusion from this experiment is that it is feasible to produce rAAV in the absence of adenovirus and that this strategy yields as much, if not more, than the conventional method.

Table 2 is a summary of the results of large-scale rAAV production using pIM45 and p5repΔ-CMVcap as helper DNAs. Notably, the yield of rAAV IU/cell increases almost 10-fold when the modified-helper is used. This result is also reflected in higher titers (both in IU/ml and particles/ml) of the purified material. Shown in the table are IU/ml determined both in the presence and absence of adenovirus (Adts149). As has been reported by others (Ferrari et al., 1996, Fisher et al., 1996), rAAV titers are approximately 1000-fold higher in the presence of an Ad infection. The particle:IU ratio of these preparations is 20–120 (IU+Ad) or $4-7 \times 10^4$ (IU–Ad). The former value is within the range previously reported (Samulski et al., 1989). While the purification procedure results in a persistent yet variable level of Adts149 contamination (from $<10^3$ IU/ml to $10^7$ IU/ml;), the stocks are free of contaminating wt AAV (see below).

TABLE 1

Comparison of Helper Plasmids Containing RSV-Rep and CMV-Cap

| SAMPLE | TITER (IU/ml)* |
| --- | --- |
| pIM45 | $6.0 \times 10^6$ |
| pIMRSV | $3.2 \times 10^5$ |
| p5repΔ-CMV cap | $5.5 \times 10^7$ |
| RSV repΔ-CMV cap | $1.0 \times 10^7$ |
| p5repΔ-p40 cap | $1.3 \times 10^6$ |
| RSV repΔ-p40 cap | $1.3 \times 10^5$ |

*Shown is the average of five separate experiments (-lowest, highest values).

| | |
| --- | --- |
| 293 (standard conditions) – Ad | 0 |
| 293 (standard conditions) + Ad | $4.3 \times 10^6$ |
| VK2-20 + E2VA 5'-->3' | |
| –induction | $5.4 \times 10^5$ |
| +induction* | $7.6 \times 10^5$ |
| VK2-20 + E2VA 3'-->5' | |
| –induction | $1.4 \times 10^5$ |
| +induction* | $7.6 \times 10^5$ |
| ORF6 lines + E2VA 5'-->3' + induction+ | |
| 3B1 | $3.4 \times 10^7$ |
| 4B1 | $4.1 \times 10^7$ |
| 3C2 | $2.6 \times 10^6$ |
| 4A6 | $8.6 \times 10^6$ |
| 2C4 | $1.4 \times 10^8$ |

*lines were induced with dexamethasone (for E4) but not with $Zn^{+2}$ (for E2).
+ORF6 and E2 expression were induced with $Zn^{+2}$ and $Cd^{+2}$

TABLE 2

Large Scale Purification of Recombinant AAV(TRlacZ)*

| | LYSATE | | FINAL | | |
| --- | --- | --- | --- | --- | --- |
| PLASMID | TITER (IU/ml + Ad) | IU/ cell | TITER (IU/ml + Ad) | TITER (IU/ml – Ad) | PARTICLES/ ML |
| pIM45 | $2.0 \times 10^8$ | 2.9 | $4.3 \times 10^7$ | $8.0 \times 10^4$ | $7.4 \times 10^9$ |
| p5repΔ CMVcap | $8.9 \times 10^8$ | 27 | $5.2 \times 10^8$ | $4.4 \times 10^5$ | $1.9 \times 10^{10}$ |

*shown are the averages of 9 preps for each helper plasmid; these were derived from the transfection of approximately $1 \times 10^9$ cells and purified via CsCl gradient centrifugation (see Methods).

H. Analysis of Replication and Levels of WTAAV Contamination

Hirt analysis was performed on samples from small-scale transient transfections such as those described above to assay replication of the vectors and to assess levels of wtAAV contamination. All of the helper DNAs supported replication of the TRlacZ vector (FIG. 15, panel A); however, in each transfection using a helper plasmid containing an RSV LTR-rep cassette, the vector appeared to replicate at a diminished level (the ethidium-bromide stained gel indicated equal amounts of DNA were loaded in each lane). This result might also help to explain the reduced viral yields obtained with the helpers containing RSV-rep. A low level of replication was observed when the amber mutant, pIMRSV-am was used as a helper, confirming, as shown in FIG. 13, panel A, that a small amount of full-length Rep protein is synthesized by this mutant. When the same blot was probed with a fragment from the wtAAV genome, no evidence of replicating wtAAV viral DNA was observed (FIG. 15, panel C). There was, however, hybridization to high molecular weight DNA in some lanes. This could represent cross-hybridization with cellular sequences bearing some homology to the wtAAV probe. However, since no signal appeared in the negative control (mock) lane, an alternative explanation might be that the signal is evidence of integration of the helper DNA into the 293 cell genome. Interestingly, this high molecular weight band appeared only in cells transfected with helpers carrying the p5-rep cassette rather than RSV LTR-rep, suggesting that overexpression of rep might inhibit integration or alternatively, that sequences within p5 (ie. the Rep-binding site or RRS) might be required in cis for integration. Lending support to the integration hypothesis is the observation that no signal appears in cells transfected with the mutant pIMRSV-am, suggesting that this phenomenon is dependent upon Rep synthesis. Lysates harvested in parallel from these transfections were used to infect a second plate of 293 cells in the presence of Adts149 and Hirt samples were prepared. If in fact a small amount of contaminating wt AAV were present, then the virus should have been amplified upon reinfection. Southern analysis and hybridization with a wtAAV probe (FIG. 15, panel D) again showed no evidence of replicating wtAAV viral DNA. When a duplicate blot was probed with a lacZ fragment (FIG. 15, panel B), no replicating vector DNA was observed. This latter result is further evidence of the lack of wt AAV since the presence of wt AAV (i.e., rep gene expression) would have allowed vector replication under these conditions.

AAV promoters in a standard helper plasmid were substituted with stronger heterologous promoters in order to enhance separately the expression of the Rep and Cap proteins required for rAAV packaging. These experiments showed that rAAV yield was improved by approximately 10-fold when cap gene expression was increased, implying that the level of capsid protein is one limiting factor for production of rAAV. In contrast, rep gene expression is probably not a limiting factor since overexpression of rep did not increase rAAV yield. However, it is not possible to make a definitive conclusion on this issue as increases in Rep protein synthesis were always coupled with reductions in capsid protein production. In the case of the plasmid pRSVrepΔ-CMVcap, however, Cap protein production was diminished only slightly relative to that observed with p5repΔ-CMVcap (at most 2-fold, but the level was still higher than attained with pIM45) while Rep78 expression was enhanced significantly (approximately 5-fold). Under these conditions, there was no increase in rAAV yield over p5repΔ-CMVcap; packaging efficiency was in fact slightly reduced. These conclusions conflict with those made based on a previous study (Flotte et al. 1995) in which use of a construct expressing rep from the HIV LTR (pHIVrep/p40cap) led to a 10-fold increase in rAAV yield compared to a construct in which p5 controlled rep expression (pAAV/Ad).

Another, related factor restricting AAV vector production by the standard protocol is transfection efficiency as the overall level of Rep and Cap protein synthesis is limited both by the number of cells taking up DNA as well as the number of DNA molecules present within each cell. In an attempt to increase transfection efficiency, plasmid DNA has been complexed to replication-competent adenovirus modified with polylysine, resulting in an increase in rAAV packaging of 40–240 fold over the standard calcium phosphate method (Mamounas et al., 1995). A number of modifications to the standard rAAV production procedure were made by Chiorini et al. (1995); instead of transfecting 293 cells with calcium phosphate, COS cells were electroporated with reported transfection efficiencies of up to 90%. The helper plasmid used for those studies also contained an SV40 replicon, presumably increasing the copy number of the rep and cap genes within each transfected cell. By this method, a packaging efficiency of over $10^3$ rAAV particles/cell was achieved. Alternatively, packaging cell lines have been constructed in order to avoid the inefficient transfection step. When vector DNA was introduced into a stable cell line, a five-fold improvement in rAAV yield over cotransfection was reported, resulting in $10^4$ particles/cell (Flotte et al., 1995). Clark et al. (1995) have constructed a cell line containing both the vector and AAV rep/cap genes which allows production of rAAV by adenovirus infection alone. This system yields 30 IU/cell (approximately 400 particles/cell), a value which is comparable to that achieved with the improved helper plasmid described here. Given the experience of others, it is likely that the packaging protocol employed in these studies can be further improved, either by replicating the helper plasmid within the transfected cell or by using the new helper construct to generate a packaging cell line.

The effect observed on Cap protein expression resulting from replacement of p5 with the RSV LTR confirmed the work of others with respect to AAV gene regulation. In addition to their function in replication, the AAV Rep proteins (primarily Rep78/68; Kyostio et al., 1994; Horer et al., 1995) are known to act as transcriptional regulators. In the absence of an adenovirus infection, Rep proteins repress transcription from AAV promoters (Tratschin et al., 1986, Trempe and Carter, 1988, Beaton et al., 1989, Kyostio et al., 1994) while conversely, they activate transcription from these promoters in response to adenovirus infection (Labow et al., 1986, Tratschin et al., 1986). McCarty et al. (1991) have shown that Rep-mediated activation of the p19 and p40 promoters in the presence of adenovirus is dependent in cis upon sequences located upstream of both p5 and p19. Consistent with this finding was the lack of induction of p40 transcription upon adenovirus infection when p5 was deleted and replaced with the RSV LTR (as in the pIMRSV plasmid). Similarly, there was also no increase in the level of p19 RNA with this construct. The failure to observe induction was due to removal of sequences required in cis since it occurred independently of rep gene expression; transcriptional activation of p40 was not restored (FIG. 4) when Rep protein synthesis was prevented by an amber mutation or when Rep protein was supplied in trans. Relative to pIM45, pIMRSV lacks only 84 bp upstream of p5 (bp 191–275 of the AAV sequence); this deletion is more limited than the one reported by McCarty et al. (1991) (bp 191–320) and thus further defines the location of the putative regulatory region required for Rep activation. The region between bp 191 and 275 is known to contain binding sites for the major late transcription factor (USF; Chang et al., 1989), YY1 (Shi et al., 1991) and Rep (McCarty et al., 1994; Kyostio et al., 1995) as well as the p5 TATA box.

Though transcription from the p40 promoter in the pIMRSV-am mutant was not activated by Rep in response to adenovirus infection, Cap protein synthesis was observed to increase. This effect may be attributed to the translational inhibitory activity of Rep. In 293 cells in the absence of an adenovirus infection, Trempe and Carter (1988) observed that the level of p40 mRNA was reduced while CAT protein expression increased in the absence of Rep compared to a rep gene-containing vector. In cells transfected with pIMRSVam, synthesis of the capsid proteins is significantly enhanced with adenovirus infection. This increase, however, occurs without any alteration in the steady-state level of p40 mRNA, indicating that it is a translational effect. In comparison, capsid protein production also increases in cells transfected with pIM45, but in this case, there is a concomitant increase in the level of both the 2.6 kb and 2.3 kb p40 mRNAs. The apparent induction in the synthesis of the capsid proteins with pIMRSVam is a trans effect of the mutation of the rep gene, as it does not occur in any case where the Rep proteins are expressed. Because Rep78 is the major Rep protein produced by pIMRSV, it is presumably the primary mediator of the inhibitory effect, however, a role for Rep68 cannot be ruled out. These results suggest that although adenovirus infection is capable of significantly increasing the efficiency of translation of p40 mRNA (West et al., 1987; Janik et al., 1989), this effect can be counteracted by the Rep proteins. It is not clear whether translational inhibition in the presence of adenovirus occurs as a normal function of Rep or if it is an artifact of overexpression of the rep gene in the pIMRSV construct. Alternatively, inhibition may occur only when the level of p40 mRNA is low and can be overcome when transcription from p40 normally increases with adenovirus infection. Induction of transcription from p40 was prevented in this case by removal of sequences upstream of p5.

These experiments have provided further evidence of the ability of the Rep proteins to act as repressors of expression from heterologous promoters. The Rep proteins are known to down-regulate expression of several heterologous genes (Labow et al., 1987; Antoni et al., 1991; Rittner et al., 1992; Oelze et al., 1994; Horer et al., 1995). In the experiments described here, expression of the cap gene from the CMV IE promoter as well as the rep gene from the RSV LTR were both down-regulated by Rep. Rep has previously been shown reduce the level of expression of the cat gene from the CMV IE promoter (Heilbronn et al., 1990); similar to the results obtained here, this effect was minor (approximately 2-fold). For both the CMV IE and RSV LTR promoters, inhibition occurred at the RNA level, though since steady-state levels of RNA were assayed by the Northern analysis, the effect could be either at the level of transcription or mRNA stability. Down-regulation at the RNA level has also been demonstrated in the case of the HIV LTR and HPV18 URR promoters and has been attributed primarily to Rep 78/68 (Antoni et al., 1991; Horer et al., 1995).

The following examples are intended to illustrate the invention without limiting the scope thereof.

EXAMPLE 1

Figure 7:
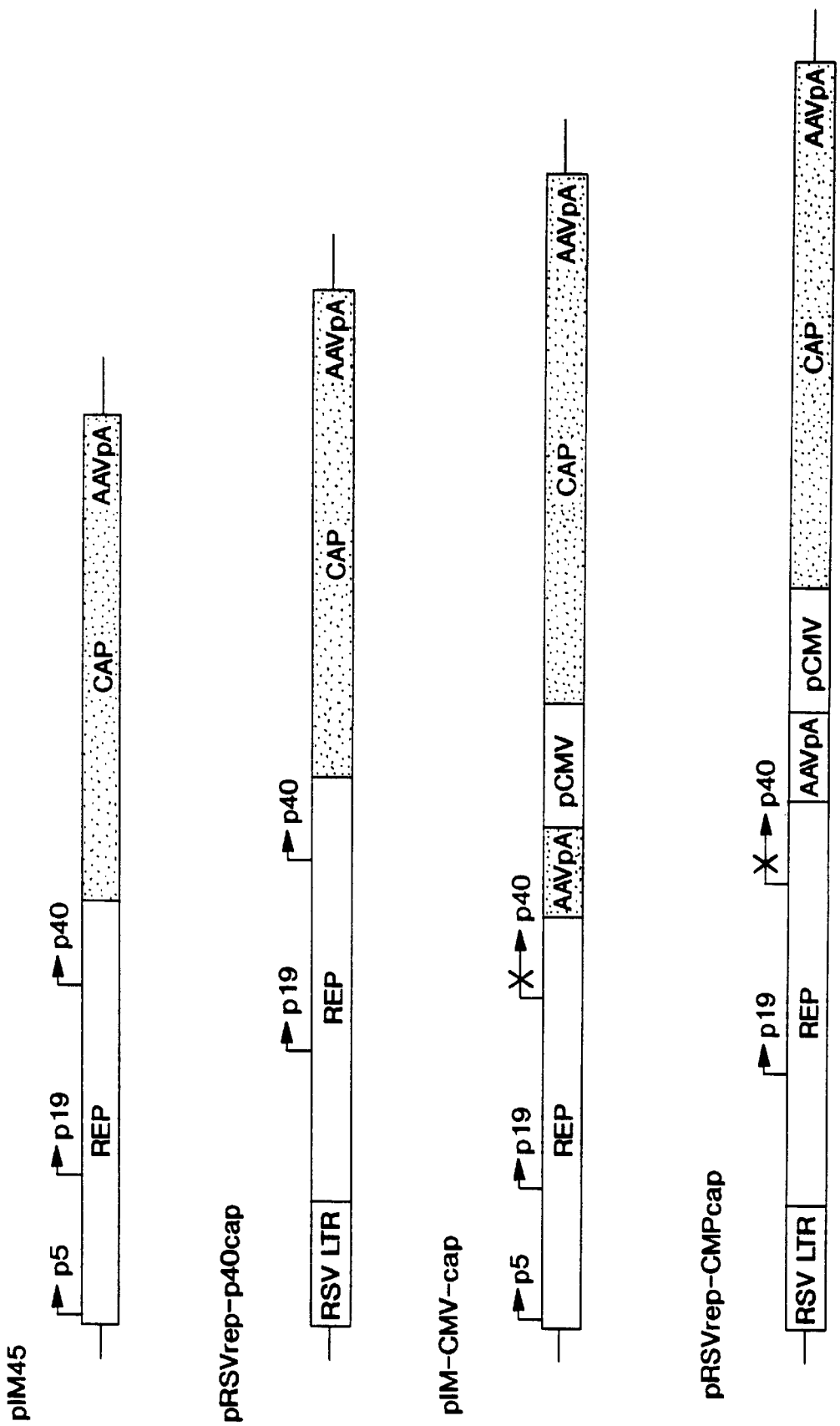
FIG. 7 shows a diagram of helper plasmids containing the AAV rep and cap genes used in AAV vector production.

Recombinant AAV Production Using a Non-replicating Helper Plasmid Containing AAV Helper Genes An experiment was performed to determine if a helper plasmid providing the AAV rep and cap genes on a nonreplicating plasmid and using heterologous promoters for gene expression would increase AAV vector titer above that derived from controls in which the rep and cap genes are expressed from their own promoters. The helper plasmids tested are shown in FIG. 7.

pIM45 contains the AAV rep and cap genes under the control of the native AAV promoters, and the AAV polyA site at the 3' end (McCarty, D. M. et al., *J.Virol.* 65:2936–2945, 1991).

pRSVrep-p40cap and pRSVrep-CMVcap were constructed by deleting the cap region from pIM45 using PCR to delete nucleotides 2287–4049 in the AAV genome, resulting in the generation of pRep*30. A PCR fragment isolated from pRep*30, nucleotides 275–4464, containing NheI and NotI ends, was cloned in between the NheI and NotI sites in pRep9 (Invitrogen, San Diego, Calif.) to make pRSVrep. An XbaI (filled in)-SfiI fragment from pRSVrep was cloned into SmaI and SfiI digested pIM45 to make pRSVrep-p40cap. This same XbaI (filled in)-SfiI fragment from pRSVrep was cloned into SmaI and SfiI digested pIM-CMVcap (see below) to make pRSVrep-CMVcap.

pIM-CMVcap was constructed by introducing 3 point mutations at positions 1823 (T:C), 1826 (A:C) and 1832 (G:A) within the AAV genome to inactivate the p40 promoter. pCMVcapB was generated by inserting a PCR fragment containing nucleotides 1850–4460 from the AAV genome and BamHI ends into the BamHI site of pCMVB (Clontech, Palo Alto, Calif.). An SphI fragment containing the CMV promoter was isolated from pCMVcapB and was inserted into the SphI site at position 930 within pIM45 to make pIM-CMVcap.

Figure 8:
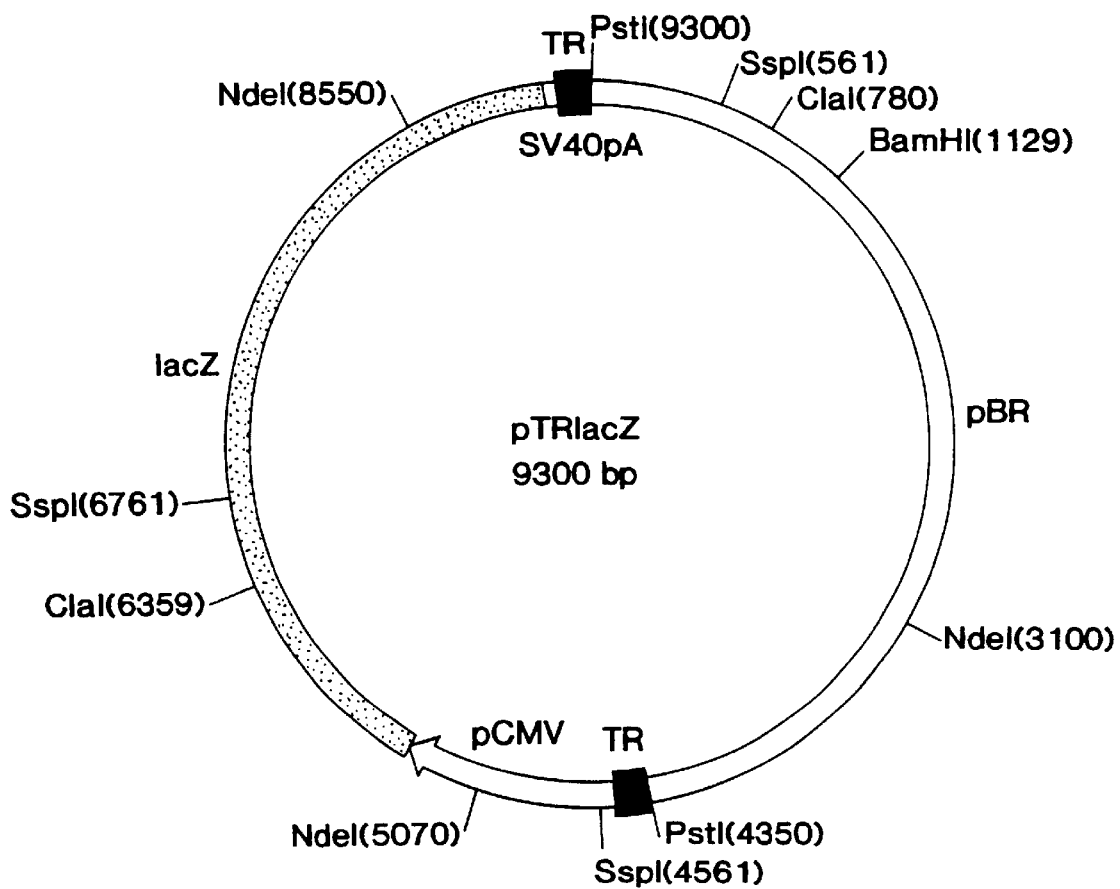
FIG. 8 shows a diagram of pTRlacZ reporter plasmid.

The helper plasmids were transfected into 293 cells at a ratio of 10:1 helper/vector (16.5 µg/total DNA). The AAV vector plasmid used was pTR-lacZ, which was developed by Dr. Nicholas Muzyczka, University of Florida. The plasmid is shown in FIG. 8. Isolation and purification of the AAV vector was performed as described in Section 4, supra.

The AAV yield was titered by coinfecting 293 cells with helper adenovirus and the AAV. This reduced the infection time, therefore increasing the sensitivity of the assay. For the titer, 293 cells were plated in 96-well plates, at $5 \times 10^5$ cells/ml. (100 µl/well) in DMEM/10% FBS (with penicillin/ streptomycin and glutamine) and allowed to grow for one day at 37° C. The cells were then coinfected with Adts149 virus using an MOI of 20, and with the AAV at dilutions of 1:100, 1:200 and 1:400 etc. of the viral preparatory stock. The different dilutions were used in order to ascertain the titer.

After the infection was allowed to progress for two days at 39° C., the medium was aspirated, the cells were incubated with 3.7% formaldehyde for 5 minutes and washed with Phosphate Buffer Saline (PBS). The cells were then stained with X-Gal (5-Bromo-4-Chloro-3-Indolyl-β-D-galactopyranoside) at 37° C. for 1–24 hours and screened for the presence of blue coloration in cells in order to detect the expression of the lacZ gene contained in the AAV vector. A conversion using the Titer Analysis program, which is based on determining the endpoint dilution, was, used for determination of the titer in IU/ml.

Figure 9:
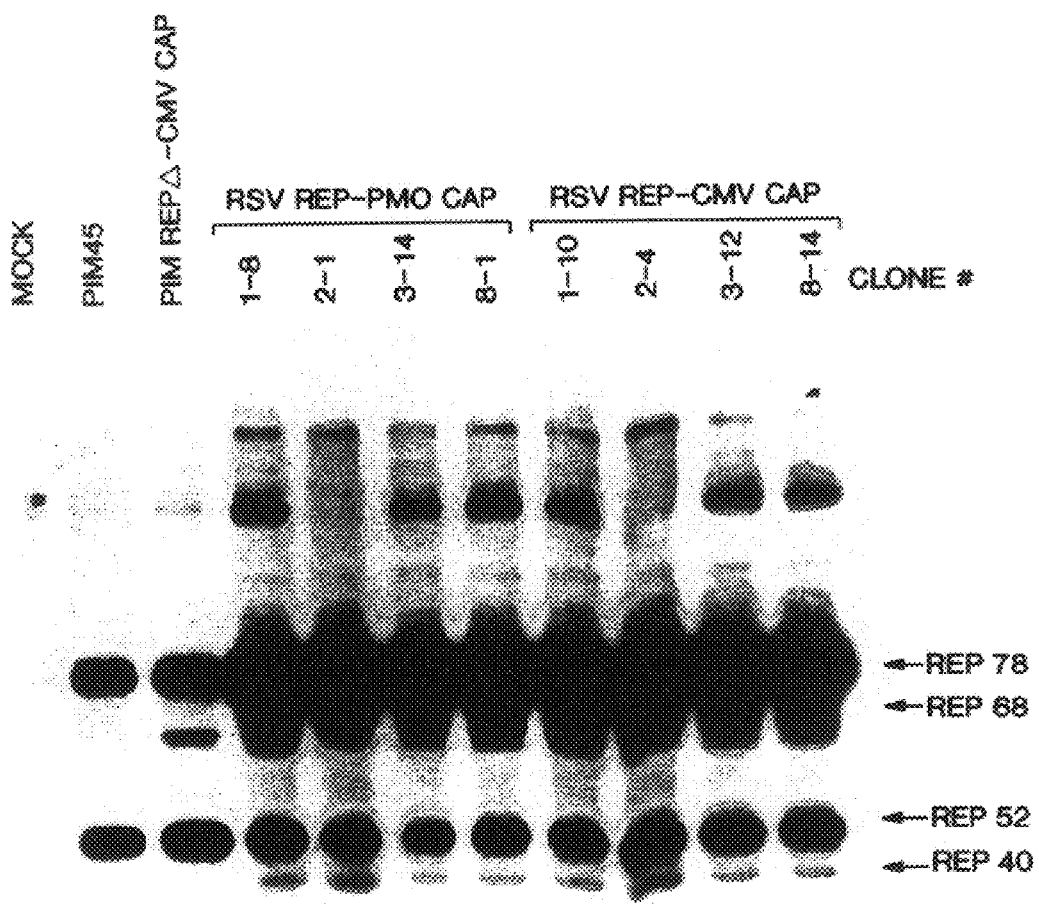
FIG. 9 shows a Western blot analysis of rep protein expression from AAV nonreplicating helper plasmids. The rep proteins (in kd) are indicated at right.
Figure 10:
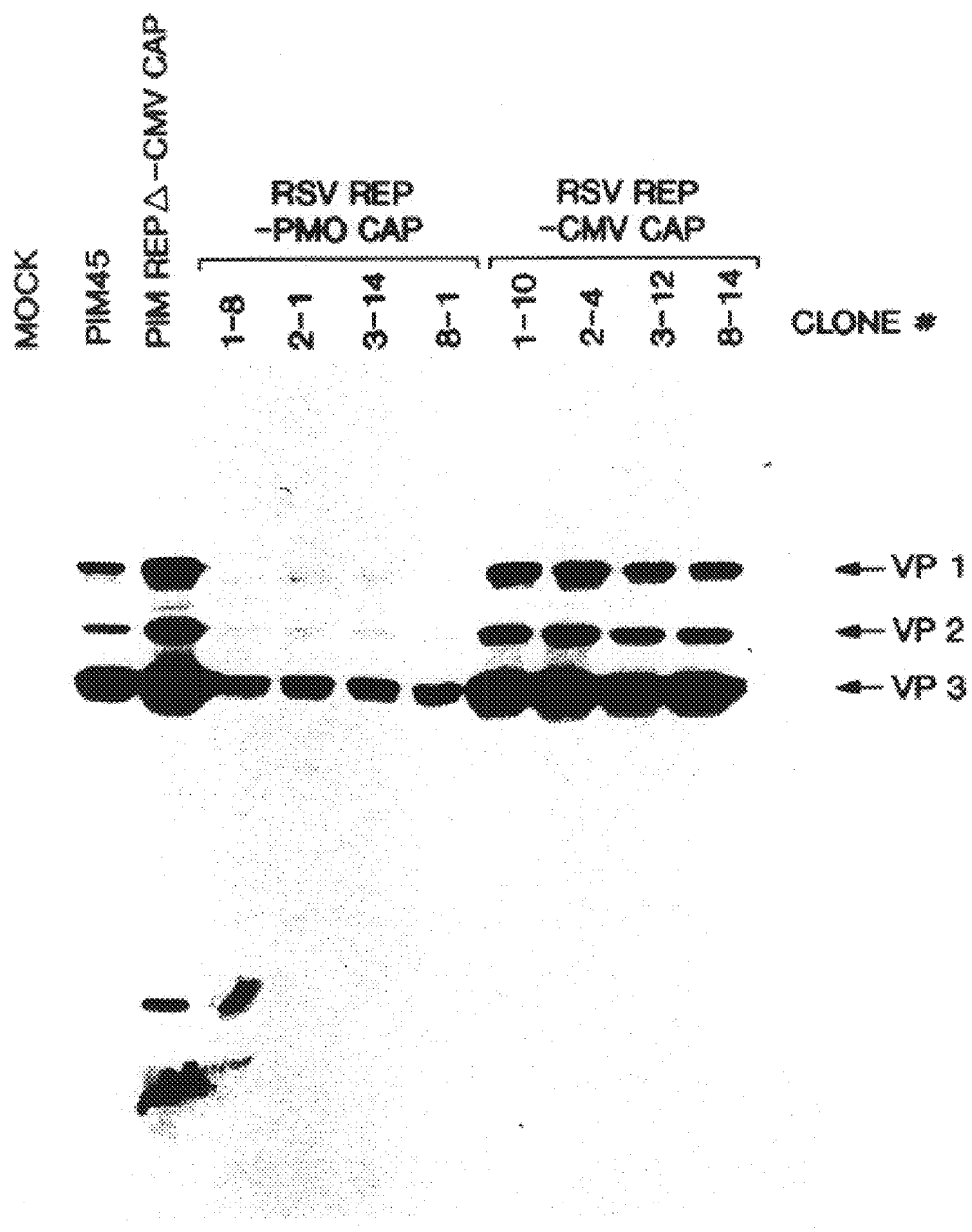
FIG. 10 shows a Western blot analysis of cap protein expression from AAV nonreplicating helper plasmids. The cap proteins (VP, in kd) are indicated at right.

A Western blot analysis was performed to determine the levels of rep and cap protein expression using the various helper plasmids (and specific clones) shown in FIG. 7. FIG. 9 shows a Western blot analysis of rep protein expression, while FIG. 10 shows a Western blot analysis of cap protein expression. Standard techniques were used in the Western blot analysis (*Current Protocols in Molecular Biology*, Ausubel, F. et al., eds., Wiley and Sons, New York, 1995).

The titer data is shown in TABLE 3. The titer of vector stock is given in IU/ml. The experiment demonstrates that increased levels of cap expression in particular, as evidenced by the Western blot, leads to increased production of the AAV vector, pTRlacZ, as evidenced by the titers shown.

TABLE 3

| COMPARISON OF HELPER PLASMIDS CONTAINING RSV-REP AND CMV-CAP:LYSATE TITERS | |
|---|---|
| SAMPLE | TITER (IU/ML) |
| mock | 0 |
| pIM45 | $1.7 \times 10^6$ |
| pIM-CMVcap | $3.2 \times 10^7$ |
| pRSVrep-p40cap clones | |
| 1-8 | $2.4 \times 10^6$ |
| 2-1 | $2.2 \times 10^5$ |
| 3-14 | $3.6 \times 10^5$ |
| 8-1 | $1.5 \times 10^5$ |
| pRSVrep-CMVcap clones | |
| 1-10 | $1.4 \times 10^7$ |
| 2-4 | $4.9 \times 10^6$ |
| 3-12 | $1.9 \times 10^7$ |
| 8-14 | $1.2 \times 10^7$ |

EXAMPLE 2

Cell Lines, Viruses and Plasmid DNA

The 293 cell line, an adenovirus 5-transformed human embryonic kidney cell line (Graham et al., 1977) was propagated in Dulbecco's modified Eagle's medium-high glucose (DME; Irvine Scientific) supplemented with 10% fetal bovine serum (FBS; Irvine Scientific, Santa Ana, Calif.), 20 mM glutamine, 100 units/ml penicillin and 100 µg/ml streptomycin (Gibco-BRL, Gaithersburg, Md.) at 37° C. and 5% $CO_2$. The adenovirus type 5 mutant, ts149 (Ad5ts149; Ensinger and Ginsberg, 1972) used as a helper virus in these studies has reduced ability to replicate viral DNA at the nonpermissive temperature (30° C.) due to a temperature-sensitive mutation in the DNA polymerase encoded by adenovirus early region 2 (Stillman et al., 1982). Ad5ts149 was grown in 293 cells at the permissive temperature (33° C.) and purified by CsCl gradient centrifugation.

Plasmid DNA encoding the recombinant AAV vector, pTRlacZ, as well as the helper plasmid, pIM45 (McCarty et al., 1991), were generously provided by N. Muzyczka (Univ. of Florida). pTRlacZ consists of the *E.coli* LacZ gene (cytoplasmic) under the transcriptional control of the CMV IE promoter, inserted between the terminal repeats of AAV. The plasmid encoding the amber suppressor tRNA, pSVtsSu$^+$ (amber) (Capone et al., 1985) was obtained from U. L. RajBhandary (MIT). pNTC3, an AAV genomic clone containing an amber mutation within the rep coding region (Chejanovsky and Carter, 1989) was kindly provided by R. Owens (NIH).

A. Plasmid Construction

Using pIM45 as the starting plasmid, the endogenous AAV promoters, p5 and p40 were replaced with the Rous Sarcoma Virus long terminal repeat (RSV LTR) and CMV IE promoter, respectively. All manipulations were carried out following standard cloning procedures (Sambrook et al., 1989). All restriction and DNA-modifying enzymes were obtained from New England Biolabs (Beverly, Mass.) and used according to the manufacturer's specifications. Plasmid DNAs were purified using kits obtained from Qiagen (Chatsworth, Calif.).

The CMV IE-cap cassette was constructed by first amplifying a DNA fragment consisting of AAV genomic sequences between bp 1852 and 4440 (encoding the capsid proteins and including the AAV mRNA polyadenylation site) via PCR (Saiki et al, 1988) using Vent polymerase (New England Biolabs, Beverly, Mass.). This fragment was inserted between the BamHI sites of pCMVβ (Clontech, Palo Alto, Calif.) to generate the plasmid pCMVcap.

To derive a minimal Rep-encoding sequence, rep gene sequences between the BamHI site (bp 1045) and ApaI site (bp 2283) were PCR-amplified and inserted within the pIM45 plasmid digested with BamHI and ApaI. The result was a deletion between bp 2283 (just downstream of the Rep termination codon) and the ApaI site at bp 4049. This plasmid, pIMrepΔ, was used to generate a construct in which Rep78/68 are expressed from the RSV LTR. A 2.4 kb rep gene fragment extending from bp 2.76 (just upstream of the Rep78/68 mRNA initiation codon) to bp 4459 was PCR-amplified from pIMrepΔ and inserted between the NheI and NotI sites of the pRep9 expression vector (Invitrogen, San Diego, Calif.) to create pRSVrep.

Because the Rep and Cap protein coding sequences overlap in the region of the AAV intron, there is 431 bp in common between the rep and cap gene cassettes (between bp 1852 and 2283) of pIMrepΔ and pCMVcap. Prior to insertion of the CMV IE-cap fragment into pIMrepΔ to create p5repΔ-CMVcap, p40 sequences within pIMrepΔ were mutated to inactivate the promoter. This was done to prevent the generation of wild-type AAV as a consequence of recombination between the shared sequences. Mutagenesis was carried out by overlap extension PCR (Higuchi et al., 1988). pIMrepΔ was used as a template for the first PCR using flanking primer-1 (5'-GGATTACCTCGGAGAAGCAGTGGATCC-3'; bp 1024–1050 of the AAV genome) and mutagenic primer-1 (5'-GTTTGGGTTCACTGATGTCTGCGTCACTG-3', AAV bp 1821–1841; mutated nucleotides are underlined). The result is the introduction of three base pair mutations in the region of the p40 TATA box: from TATAAGTGAG to CATCAGTGAA. The G to A change ablates a BanII site to enable screening by restriction analysis. pIMrepΔ was also used as a template for the second PCR using flanking primer-2 (5'-GTGTGGAATCTTTGCCCAGATGGGCCCGGTTT-GAGCTTC-3'; AAV bp 2260–2283, 4049–4066) and mutagenic primer-2 (5'-CAGTGACGCAGACATCAGTGAACCCAAACG-3'; AAV bp 1821–1841). After gel purification of the above PCR products, a third PCR was performed by annealing the two earlier products and carrying out a final amplification step using only the flanking primers, thereby generating a 1285 bp DNA fragment. This fragment was digested with BamHI and ApaI and cloned into the corresponding sites of the pIMrepΔ backbone. The resulting plasmid was pIMrepΔ/p40Δ. The helper plasmid p5repΔ-CMVcap was constructed by inserting a SphI fragment from pCMVcap containing the CMV IE promoter and cap gene cassette into the unique SphI site of pIMrepΔ/p40Δ. Similarly, in order to construct p5repΔ-p40cap, a PCR fragment with SphI ends extending from AAV bp 1715 to 4461 was generated from pIM45 and cloned into the SphI site of pIMrepΔ/p40Δ.

The p5 promoter regions in the plasmids pIM45, p5repΔ-CMVcap and p5repΔ-p40cap were replaced with the RSV LTR promoter by first cleaving pRSVrep with XbaI. The XbaI site was made blunt with DNA PolymeraseI-Klenow fragment and the DNA was restricted with SfiI to release a fragment containing the RSV promoter and the 5' end of the rep gene. This fragment was then cloned between the SmaI and SfiI sites of the parental plasmid.

To introduce an amber mutation into pIMRSV, a SfiI-BamHI fragment containing the mutation (at bp 1033 of the AAV genome) was isolated from the plasmid pNTC3 (Chejanovsky and Carter, 1989) and cloned into the corresponding sites of pIMRSV.

EXAMPLE 3

Transient Transfections and Analysis of rAAV Replication and Packaging

For small-scale experiments, 293 cells were seeded at a density of $1 \times 10^6$ cells per 6 cm dish 48 hours before transfection. The cells were infected with Ad5ts149 in DME-10% FBS at a multiplicity of infection (MOI) of 20 for 1 hour at 37° C. prior to transfection. Transfection procedures were carried out using the calcium phosphate ProFection kit (Promega, Madison, Wiss.) according to manufacturer's instructions. In general, for rAAV packaging, each dish received a mix of 1.5 $\mu$g vector DNA (i.e. pTRlacZ) and 15 $\mu$g of helper DNA. Following incubation at 37° C. for 5 hours, the infection/transfection was terminated by replacing the media with fresh DME-10% FBS; the dishes were then transferred to 39° C. (the non-permissive temperature for Ad5ts149).

For analysis of rAAV packaging, cells were harvested at 48 hours post-transfection by low-speed centrifugation in a clinical centrifuge. The pellet from each dish was resuspended in 100 $\mu$l phosphate-buffered saline (PBS) and freeze-thawed four times to liberate the rAAV. Adenovirus was heat-inactivated by incubating the lysate at 56° C. for 30 minutes. The lysate was subjected to a second low-speed spin to pellet cellular debris and the supernatant was collected. The rAAV titer was determined on 293 cells (+/− coinfection with Ad5ts149; MOI=20) by endpoint dilution. Following staining of the cells with X-gal (5-bromo-4-chloro-3-indoyl-β-D-galacto-pyranoside) for 20–24 hours, titers were calculated using a computer program based on Karber's method (Lynn, 1992).

Replication of vector DNA in transfected cells was assayed by isolating extrachromosomal DNA 48 hours post-transfection according to the Hirt fractionation method (Hirt, 1967). DNAs were restricted with DpnI (to digest input DNA) prior to agarose gel electrophoresis and Southern analysis. The lacZ and wild-type AAV probes used were both 50-mer oligonucleotides, 5'- ACTGCTGCCAG-GCGCTGATGTGCCC GGCTTCTGACC ATG CGGTCGCGTTC-3' and 5'-TCGGAGGAAGCAAGGT-GCGCGTGGACC AGAAATGCAAG TCCTCGG CCCAG-3' (AAV nucleotides 1501–1550), respectively. These were labelled with [$\gamma$-$^{32}$P] ATP using T4 polynucleotide kinase according to standard procedures (Sambrook et al., 1989). The filter was hybridized and washed as described below for the Northern blot analysis, except that the prehybridization, hybridization and final wash step were at 60° C.

A. Protein Extraction and Immunoblotting

For analysis of Rep and Cap protein expression from the various helper plasmids, 293 cells were first transfected as described above. Nuclear fractions were prepared 48 hours post-transfection according to the procedure described by Mendelson et al. (1986). Sample volumes were normalized according to DNA content (by optical density at 260 nm), mixed with 15–20 $\mu$l of sample buffer (500 mM Tris-HCl, pH 6.8, 10% sodium dodecyl sulfate (SDS), 20 mM EDTA, 10% β-mercaptoethanol, 10% glycerol, and 0.2% bromophenol blue), and boiled for 5 minutes prior to loading.

Following electrophoresis in 10% polyacrylamide/0.1% SDS gels, proteins were transferred from the gel to Hybond polyvinylidene difluoride (Amersham, Arlington Heights, Ill.) membranes. Prior to staining, the filters were blocked for 1 hour at room temperature in 5% milk powder dissolved in TBST (10 mM Tris HCl, pH 8.0, 150 mM NaCl and 0.05% Tween 20). The primary antibodies used for Rep and Cap Westerns were both mouse monoclonals (American Research Products, Belmont, Mass.): anti-AAV Rep protein, 303.9 (used at a dilution of.1:10 in TBST) and anti-VP1, VP-2 and VP-3 of AAV, B1 (used at a dilution of 1:5 in TBST), respectively. These were incubated on the filter for 2 hours at room temperature with vigorous shaking. Following a wash step in TBST (3×15 minutes), the filter was incubated in the secondary antibody, goat anti-mouse IgG (Fab-specific) peroxidase conjugate (Sigma, St. Louis, Mo.), for 1 hour at room temperature. The filter was then washed as before and developed using the ECL kit (Amersham).

B. Isolation of RNA and Northern Analysis

Total RNA was isolated from transfected 293 cells using RNAzol B (Tel-Test, Inc., Friendswood, Tex.) according to the manufacturer's instructions. Prior to electrophoresis, 10 $\mu$g of each RNA was combined with denaturation cocktail (50% DMSO, 10% formaldehyde, 20 mM MOPS (morpholinepropanesulfonic acid), pH 7.0, 10 mM sodium acetate, 1 mM EDTA) and loading dyes (5% glycerol, 0.1 mM EDTA, 0.04% bromophenol blue, 0.04% xylene cyanol) and heated at 65° C. for 15 minutes. Electrophoresis was through a 1% agarose/0.65% formaldehyde gel assembled and run in MOPS running buffer (20 mM MOPS, pH 7.0, 10 mM sodium acetate, 1 mM EDTA). Transfer to GeneScreen nylon membrane (NEN-DuPont, Boston, Mass.) was carried out by capillary action overnight in 10×SSC (1.5 M NaCl, 0.15 M sodium citrate; Sambrook et al., 1989).

The filters were prehybridized for 4–5 hours at 65° C. and then hybridized with probe overnight at 65° C. in hybridization buffer (5×SSC, 0.5% SDS, 5×Denhardt's solution (Sambrook et al., 1989), 100 $\mu$g/ml denatured salmon sperm DNA). The probe was a 1.6 kb HincII fragment of pIM45 (AAV bp 2397 to 3987) labelled with [$\alpha$-$^{32}$P]dATP (specific activity, 3,000 Ci/mmol; NEN-DuPont, Boston, Mass.) using a random primer labelling kit (Stratagene, La Jolla, Calif.). The filter was washed for 5 minutes at room temperature in 2×SSC, 0.5% SDS, 15 minutes at room temperature in 2×SSC, 0.1% SDS, and then for 2 hours in 0.1×SSC, 0.5% SDS at 65° C. and exposed to film.

C. Large-Scale Transfection and rAAV Purification

Prior to transfection of 293 cells for large-scale growth of rAAV the cells were seeded in roller bottles such that they would reach 60–80% confluence on the day of transfection (final density was approximately $1 \times 10^8$ cells/bottle). Transfection was carried out in OptiMem media (Gibco-BRL Life Technologies, Gaithersburg, Md.) using lipid #53:DOPE (Lee et al., 1996), 22 $\mu$g of vector DNA and 218 $\mu$g of helper DNA per bottle. Cells were infected with Ad5ts149 at a MOI of 20 at the time of transfection and incubated at 39° C. for 48 hours prior to harvest.

At the time of harvest, cells were dislodged from the bottles by gentle shaking. The cells were pelleted by centrifugation in a Sorvall RC-3B swinging bucket rotor (2500 rpm, 4° C., 15 minutes) and frozen. For purification of rAAV, the cells were resuspended in PBS containing 2 mM MgCl$_2$, 0.7 mM CaCl$_2$, 10% glycerol, and 0.1% Tween. Benzonase® (Nycomed Pharma A/S, Copenhagen, Denmark) was added (10 $\mu$l/$1 \times 10^8$ cells) and the suspension was incubated with shaking for 1 hour at room temperature. Trypsin (Gibco-BRL Life Technologies) was added to a final concentration of 0.25% and the suspension was incubated again with shaking for 1 hour at room temperature. The cell debris was collected by centrifugation (3000 rpm, 15 minutes, 4° C. in Sorvall RC-3B) and the lysate was filtered through a 0.45 $\mu$M filter.

The lysate was then subjected to centrifugation through a CsCl step gradient (4 hours, 26K rpm, 4° C., SW28 rotor) in which the top and bottom layers were 1.37 g/ml and 1.5 g/ml CsCl, respectively. The top layer was collected (between the CsCl interface and the Ad5ts149 band), adjusted to 1.41 g/ml CsCl, and centrifuged through a 1.41 g/ml CsCl equilibrium gradient (16–20 hours, 4° C., 35,000 rpm, NVT.65 rotor). Fractions were collected and assayed on a refractometer; fractions with a density of 1.36–1.41 were pooled and dialyzed against PBS/1% sucrose for 6 hours at 4° C. Sucrose was added to a final concentration of 5% and the purified virus was stored in aliquots at −80° C.

D. Characterization of Purified rAAV Stocks

The purified rAAV stock was titered for rAAV in the presence and absence of Ad5ts149 (MOI=20) by endpoint dilution as described above. The titer of contaminating Ad5ts149 was determined in a similar manner except staining was for hexon using anti-adenovirus (hexon)/FITC conjugate (Chemicon, Temecula, Calif.). The level of contaminating wild-type AAV was assayed using the infectious center assay as described (Einerhand et al., 1995).

AAV particle titer was quantitated using a procedure modified from Samulski et al. (1989). The purified rAAV sample was first treated with proteinase K in 0.1% SDS at 37° C. for 3 hours. Appropriate dilutions as well as standard curve DNAs (for TRlacZ virus, pTRlacZ DNA was used as a standard) were treated with denaturation solution (0.5 M NaOH, 1.5 M NaCl) for 10 minutes at room temperature and a 1 ml volume was applied to a GeneScreen Plus (Amersham) membrane using a slot blot apparatus (Schleicher and Schuell, Keene, N.H.). After loading, the slot was washed with 300 $\mu$l of 0.5 M ammonium acetate, pH 5.2. The filter was dried and hybridized as described above. The probe (a PvuII fragment of pTRlacZ) was labelled using the Prime-It Fluor labelling kit (Stratagene, La Jolla, Calif.). Following a series of washes as described above (except the final wash at 65° C. was for 10 minutes), the filter was developed with the Illuminator detection kit (Stratagene). Particle concentrations were estimated by comparing the sample signal with that of the standard curve.

EXAMPLE 4

Generation of Cell Lines

293-MT-DBP

Plasmid Construction. The parental plasmid pREP-7 (Invitrogen, San Diego, Calif.), contains the EBV origin of replication and the EBNA-gene for plasmid extrachromosomal maintenance and the hygromycin resistance gene for DNA selection. To construct pREP/MT/DBP, the RSV promoter of pREP-7 was replaced with the metallothionein (MT) promoter, which is induced by heavy metals. The E2A gene encoding DNA binding protein (DBP) was cloned downstream of the MT promoter.

Generation of 293/MT/DBP Cell Line. 293 cells were transfected with pREP/MT/DBP clone 0.5 via calcium phosphate transfection. Transfected cells were selected for 6.weeks with hygromycin; selected cells were clonally expanded and judged on the basis of DBP expression (via immunofluorescence) after induction and ability to complement E1-/E2A vectors.

3B1 and 2C4 Cell Lines

The parental plasmid contains an expression cassette for adenovirus E4 6 and 6/7 open reading frames (ORFs). The promoter used to drive expression is a mutant human metallothionein promoter which has a low level basal activity. (Makarov et al., *Nuc. Acids Res.* 22(8):1504–1505 (1994)).

Both 3B1 and 2C4 cell lines were derived from 293 cells which are human embryonic-kidney cells that have been transformed with the E1 region of Adenovirus Type 2. Both 3B1 and 2C4 have the ability to complement recombinant adenovirus vectors that are deleted for E1 and E4. The cell lines contain a mutant human metallothionein promoter and SV40 splice and polyadenylation signals to drive expression of adenovirus type 2 E4 open reading frames 6 and 6/7 (adenovirus nucleotides 34082–32913). For complementation of E4 functions, the expression of ORFs 6 and 6/7 can be induced by the addition of 100 $\mu$M $Zn^{2+}$, 2 $\mu$M $Cd^{2+}$. Briefly, 293 cells were transfected with the parental plasmid. The cells were cotransfected with pSV2Neo so that individual clones could be selected with G418.

EXAMPLE 5

Transgenic Mice with AAVS1 Integration Locus

Characterization of a preferred site on human chromosome 19 for integration of adeno-associated virus DNA by non-homologous recombination. 700–800 CD-1 mice were injected with a purified DNA fragment (0.7 kb EcoRI-SacI fragment of AAVS1; Kotin et al., *EMBO J.* 11:5071–5078). 550–600 eggs survived and were cleaved. 19 mice were implanted with injected eggs and 148 pups were born.

Chromosomal DNA was isolated from mouse tails and was screened by Southern analysis. Six positive mice were found (#66, 73, 85, 93, 123, 147) (Table 4).

TABLE 4

Screening of $F_0$ mice

| Mouse # | Copy # | Sex | Restriction Enzyme(s) |
|---|---|---|---|
| 66 | <5 | male | AvaI |
| 73 | <5 | female | AvaI, BamHI |
| 85 | <5 | male | AvaI, BamHI |
| 93 | <5 | female | AvaI |
| 123 | 10–20 | female | AvaI |
| 147 | <5 | female | AvaI |

Note:
Copy # estimated due to probable mosaic nature of mice

Positive Fo were mated with wt CD-1 mice and produced seventy-two F1 pups. Chromosomal DNA from F1 progeny was isolated and was screened using PCR (250 bp fragment produced by positive samples in the presence of DMSO) (Table 5). Based on the results of the screening, a total of 43 mice were kept (Table 6).

TABLE 5

Screening of F1 progeny

| $F_0$ | Sex | # of pups | Positive by PCR Total | Sex: # | (%) | Negative Kept Total | Sex: # |
|---|---|---|---|---|---|---|---|
| #66 | M | 27 | 9 | F: 6 | (33) | 2 | F: 1 |
|  |  |  |  | M: 3 |  |  | M: 1 |
| #73 | F | 14 | 11 | F: 6 | (79) | 2 | F: 1 |
|  |  |  |  | M: 5 |  |  | M: 1 |
| #85 | M | 5 | 4 | F: 0 | (80) | 1 | M: 1 |
|  |  |  |  | M: 4 |  |  |  |
| #123 | F | 12 | 5 | F: 1 | (29) | 3 | F: 1 |
|  |  |  |  | M: 4 |  |  | M: 2 |
| #147 | F | 14 | 4 | F: 3 | (29) | 2 | F: 1 |
|  |  |  |  | M: 1 |  |  | M: 1 |
| TOTAL | 6 | 72 | 33 |  |  | 10 |  |

TOTAL # MICE KEPT = 43 (pos. + and neg. −)

TABLE 6

| AAV-1-66 M Offspring # (Sex) +/− | AAV-1-73 F Offspring # (Sex) +/− | AAV-1-85 M Offspring # (Sex) +/− | AAV-1-123 F Offspring # (Sex) +/− | AAV-1-147 F Offspring # (Sex) +/− |
|---|---|---|---|---|
| 149 (F) − | 176 (F) + | 190 (M) + | 195 (M) − | 205 (M) − |
| 154 (F) + | 177 (F) + | 191 (M) + | 196 (M) + | 208 (M) + |
| 155 (F) + | 178 (F) + | 192 (M) − | 197 (M) − | 211 (F) + |
| 157 (F) + | 179 (F) + | 193 (M) + | 200 (M) + | 212 (F) + |
| 159 (M) − | 180 (F) − | 194 (M) + | 201 (M) + | 213 (F) + |
| 164 (M) + | 181 (F) + |  | 202 (F) + | 214 (F) − |
| 165 (M) + | 182 (F) + |  | 203 (F) − |  |
| 170 (M) + | 183 (M) − |  |  |  |
| 171 (F) + | 184 (M) + |  |  |  |
| 172 (F) + | 186 (M) + |  |  |  |
| 174 (F) + | 187 (M) + |  |  |  |
|  | 188 (M) + |  |  |  |
|  | 189 (M) + |  |  |  |

A. Establishment of Primary Cultures from F1 Transgenics

Briefly, tail samples were chopped and trypsinized as with previous samples. Free cells and cell chunks were placed 6-well dishes (one well/tail) in 10% calf serum in DMEM. Analysis of cell 4 days after indicated several attached cells had a fibroblast-like morphology. At that point the cell chunks were removed and replaced with fresh media. Cells from the primary F1 cultures are infected with AAV (10 MOI) (AAV titer 9×10E9/ml=9×10E6/ul) (1×$10^6$ cell/plate). 48 hours post-infection cells are harvested and subjected to Hirt analysis.

TABLE 7

Evaluation of Chromosomal Integration

| | | INTEGRATION LOCUS | |
|---|---|---|---|
| MOUSE # (SEX) | PARENT | Positive + | Negative − |
| 164 (M) | AAV-1-66 | + | |
| 165 (M) | | + | |
| 159 (M) | | | − |
| 184 (M) | AAV-1-73 | + | |
| 186 (M) | | + | |
| 190 (M) | AAV-1-85 | + | |
| 191 (M) | | + | |
| 196 (M) | AAV-1-123 | + | |
| 199 (M) | | + | |
| 195 (M) | | | − |
| 208 (M) | AAV-1-147 | + | |
| 211 (F) | | + | |

Although the invention has been described with reference to the disclosed embodiments, it should be understood that various modifications can be made without departing from the spirit of the invention. Accordingly, the invention is limited only by the following claims.

REFERENCES

Antoni, B. A., A. B. Rabson, I. L. Miller, J. P. Trempe, N. Chejanovsky and B. J. Carter. 1991. Adeno-associated virus Rep protein inhibits human immunodeficiency virus type 1 production in human cells. J. Virol. 65:396–404.

Beaton, A., P. Palumbo and K. I. Berns. 1989. Expression from the adeno-associated virus p5 and p19 promoters is negatively regulated in trans by the rep protein. J. Virol. 63:4450–4454.

Berns, K. I. and R. M. Linden. 1995. The cryptic life style of adeno-associated virus. BioEssays 3:237–245.

Blacklow, N. R., M. D. Hoggan, A. Z. Kapikian, J. B. Austin, and W. P. Rowe. 1968. Epidemiology of adeno-associated virus infection in a nursery population. Am. J. Epidemiol. 8:368–378.

Capone, J. P., P. A. Sharp, and U. L. RajBhandary. 1985. Amber, ochre and opal suppressor tRNA genes derived from a human serine tRNA gene. EMBO J. 4: 213–221.

Carter, B. J. 1992. Adeno-associated virus vectors. Curr. Opin. Biotech. 3:533–539.

Chang, L.-S., Y. Shi and T. Shenk. 1989. Adeno-associated virus p5 promoter contains an adenovirus E1A inducible element and a binding site for the major late transcription factor. J. Virol. 63:3479–3488.

Chejanovsky, N. and B. J. Carter. 1989. Replication of a human parvovirus nonsense mutant in mammalian cells containing an inducible amber suppressor. Virology 171: 239–247.

Cheung, A. K. M., M. D. Hoggan, W. W. Hauswirth and K. I. Berns. 1980. Integration of the adeno-associated virus genome into cellular DNA in latently infected human Detroit 6 cells. J. Virol. 33:739–748.

Chiorini, J. A., C. M. Wendtner, E. Urcelay, B. Safer, M. Halles, and R. M. Kotin. 1995. High-efficiency transfer of the T cell co-stimulatory molecule B7-2 to lymphoid cells using high-titer recombinant adeno-associated virus vectors. Human Gene Therapy 6:1531–1541.

Clark, K. R., F. Voulgaropoulou, D. M. Fraley and P. R. Johnson. 1995. Cell lines for the production of recombinant adeno-associated virus. Human Gene Therapy 6:1329–1341.

Einerhand, M. P. W., M. Antoniou, S. Zolotukhin, N. Muzyczka, K. I. Berns, F. Grosveld, and D. Valerio. 1995. Regulated high-level human β-globin gene expression in erythroid cells following recombinant adeno-associated virus-mediated gene transfer. Gene Therapy 2:336–343.

Ensinger, M. J. and H. S. Ginsberg. 1972. Selection and preliminary characterization of temperature-sensitive mutants of type 5 adenovirus. J. Virol. 10:328–339.

Ferrari, F. K., T. Samulski, T. Shenk and R. J. Samulski. 1996. Second-Strand synthesis is a rate-limiting step for efficient transduction by recombinant adeno-associated vrus vectors. J. Virol. 70:3227–3234.

Fisher, K. J., G.-P. Gao, M. D. Weitzman, R. DeMatteo, J. F. Burda, and J. M. Wilson. 1996. Transduction with recombinant adeno-associated vrus for gene therapy is limited by leading-strand synthesis. J. Virol. 70: 520–532.

Flotte, T. R., S. A. Afione, C. Conrad, S. A. McGrath, R. Solow, H. Oka, P. L. Zeitlin, W. B. Guggino and B. J. Carter. 1993. Stable in vivo expression of the cystic fibrosis transmembrane regulator with an adeno-associated virus vector. Proc. Natl. Acad. Sci. USA 90:10613–10617.

Flotte, T. R. and B. J. Carter. 1995. Adeno-associated virus vectors for gene therapy. Gene Therapy 2:357–362.

Flotte, T. R., X. Barraza-Ortiz, R. Solow, S. A. Afione, B. J. Carter ad W. B. Guggino. 1995. An improved system for packaging recombinant adeno-associated virus vectors capable of in vivo transduction. Gene Therapy 2:29–37.

Graham, F. L., J. Smiley, W. C. Russell, and R. Nairn. 1977. Characteristics of a human cell line transformed by DNA from human adenovirus type 5. J. Gen. Virol. 36:59–74.

Halbert, C. L., I. E. Alexander, G. M. Wolgamot, and A. D. Miller. 1995. Adeno-associated vectors transduce primary cells much less efficiently than immortalized cells. J. Virol. 69:1473–1479.

Handa, H., K. Shiroki, and H. Shimojo. 1977. Establishment and characterization of KB cell lines latently infected with adeno-associated virus type 1. Virology 82:84–92.

Heilbronn, R., A. Burkle, S. Stephan and H. zur Hausen. 1990. The adeno-associated virus rep gene suppresses herpes simplex virus-induced DNA amplification. J. Virol. 64:3012–3018.

Higuchi, R., B. Krummel, and R. K. Saiki. 1988. A general method of in vitro preparation and specific mutagenesis of DNA fragments: study of protein and DNA interactions. Nuc. Acids. Res. 16:7351–7367.

Hirt, B. 1967. Selective extraction of polyoma DNA from infected mouse cell cultures. J. Mol. Biol. 26:365–369.

Holscher, C., M. Horer, J. A. Kleinschmidt, H. Zentgraf, A. Burkle and R. Heilbronn. 1994. Cell lines inducibly expressing the adeno-associated virus (AAV) rep gene: requirements for productive replication of rep-negative mutants. J. Virol. 68:7169–7177.

Holscher, C., J. A. Kleinschmidt and A. Burkle. 1995. High-level expression of adeno-associated virus (AAV) Rep78 or Rep68 protein is sufficient for infectious particle formation by a rep-negative AAV mutant. J. Virol. 69:6880–6885.

Horer, M., S. Weger, K. Butz, F. Hoppe-Seyler, C. Geisen and J. A. Kleinschmidt. 1995. Mutational analysis of adeno-associated virus Rep protein-mediated inhibition of heterologous and homologous promoters. J. Virol. 69:5485–5496.

Janik, J. E., M. M. Huston, K. Cho and J. A. Rose. 1989. Efficient synthesis of adeno-associated virus structrual proteins requires both adenovirus DNA binding portein and VA1 RNA. Virology 168:320–329.

Kaplitt, M. G., P. Leone, R. J. Samulski, X. Xiao, D. W. Pfaff, K. L. O'Malley and M. J. During. 1994. Long-term gene expression and phenotypic correction using adeno-associated virus vectors in the mammalian brain. Nature Genetics 8:148–153.

Kotin, R. M., M. Siniscalco, R. J. Samulski, X. Zhu, L. Hunter, C. A. Laughlin, S. McLaughlin, N. Muzyczka, M. Rocchi, and K. I. Berns. 1990. Site-specific integration by adeno-associated virus. Proc. Natl. Acad. Sci. USA 87:2211–2215.

Kotin, R. M. 1994. Prospects for the use of adeno-associated virus as a vector for human gene therapy. Hum. Gene Therapy 5:793–801.

Kyostio, S. R. M., R. A. Owens, M. D. Weitzman, B. A. Antoni, N. Chejanovsky and B. J. Carter. 1994. Analysis of adeno-associated virus (AAV) wild-type and mutant Rep proteins for their abilities to negatively regulate AAV p5 and p19 mRNA levels. J. Virol. 68:2947–2957.

Kyostio, S. R. M., R. S. Wonderling and R. A. Owens. 1995. Negative regulation of the adeno-associated virus (AAV) p5 promoter involves both the p5 Rep binding site and the consensus ATP-binding motif of the AAV Rep68 protein. J. Virol. 69:6787–6796.

Labow, M. A., P. L. Hermonat and K. I. Berns. 1986. Positive and negative autoregulation of adeno-associated virus type 2 genome. J. Virol. 60:251–258.

Labow, M. A., L. H. Graf and K. I. Berns. 1987. Adeno-associated virus gene expression inhibits cellular transformation by heterologous genes. Mol. Cell. Biol. 7:1320–1325.

Laughlin, C. A., C. B. Cardellichio and J. C. Coon. 1986. Latent infection of KB cells with adeno-associated virus type 2. J. Virol. 60: 515–524.

Lebkowski, J. S., M. M. McNally, T. B. Okarma and L. B. Lerch. 1988. Adeno-associated virus: a vector system for efficient introduction and integration of DNA into a variety of mammalian cell types. Mol. Cell. Biol. 8: 3988–3996.

Lee, E. R., J. Marshall, C. S. Siegel, C. Jiang, N. S. Yew, M. R. Nichols, J. B. Nietupski, R. J. Ziegler, M. Lane, K. X. Wang, N. C. Wan, R. K. Scheule, D. J. Harris, A. E. Smith and S. H. Cheng. 1996. Detailed analysis of structures and formulations of cationic lipids for efficient gene transfer to the lung. Hum. Gene Ther. in press.

Lynn, D. E. 1992. A BASIC computer program for analyzing endpoint assays. BioTechniques 12:880–881.

Mamounas, M., M. Leavitt, M. Yu, and F. Wong-Staal. 1995. Increased titer of recombinant AAV vectors by gene transfer with adenovirus coupled to DNA-polylysine complexes. Gene Therapy 2:429–432.

McCarty, D. M., M. Christensen and N. Muzyczka. 1991. Sequences required for coordinate induction of adeno-associated virus p19 and p40 by Rep protein. J. Virol. 65:2936–2945.

McCarty, D. M., D. J. Periera, I. Zolotukhin, X. Zhou, J. H. Ryan, and N. Muzyczka. 1994. Identification of linear DNA sequences that specifically bind the adeno-associated virus Rep protein. J. Virol. 68:4988–4997.

McLaughlin, S. K., P. Collis, P. L. Hermonat and N. Muzyczka. 1988. Adeno-associated virus general transduction vectors: Analysis of proviral structures. J. Virol. 62:1963–1973.

Mendelson, E., J. P. Trempe and B. J. Carter. 1986. Identification of the trans-acting Rep Proteins of adeno-associated virus by antibodies to a synthetic oligopeptide. J.Virol. 60: 823–832.

Muzyczka, N. 1992. Use of adeno-associated virus as a general transduction vector for mammalian cells. Curr Top. Microbiol. Immunol. 158:97–129.

Oelze, I., K. Rittner and G. Sczakiel. 1994. Adeno-associated virus type 2 rep gene-mediated inhibition of basal gene expresion of human immunodeficiency virus type 1 involves its negative regulatory functions. J. Virol. 68:1229–1233.

Podsakoff, G., Wong, K. K. and S. Chatterjee. 1994. Efficient gene transfer into nondividing cells by adeno-associated virus-based vectors. J. Virol. 68:5656–5666.

Rittner, K., R. Heilbronn, J. A. Kleinschmidt and G. Sczakiel. 1992. Adeno-associated virus type2-mediated inhibition of human immunodeficiency virus type 1 (HIV-1) replication: involvement of p78$^{rep}$/p68$^{rep}$ and the HIV-1 long terminal repeat. J. Gen. Virol. 73:2977–2981.

Russell, D. W., A. D. Miller and I. E. Alexander. 1994. Adeno-associated virus vectors preferentially transduce cells in S phase. Proc. Natl. Acad. Sci. USA 91: 8915–8919.

Saiki, R. K., D. H. Gelfand, S. Stoffer, S. J. Scharf, R. Higuchi, G. T. Horn, K. B. Mullis, and H. A. Erlich. 1988. Primer-directed enzymatic amplification of DNA with a thermostable DNA polymerase. Science 239: 487–491.

Sambrook, J., E. F. Fritsch, and T. Maniatis. 1989. Molecular cloning: a laboratory manual, 2nd ed. Cold Spring Harbor Laboratory, Cold Spring Harbor, N.Y.

Samulski, R. J., L.-S. Chang, and T. Shenk. 1989. Helper-free stocks of recombinant adeno-associated viruses: normal integration does not require viral gene expression. J. Virol. 63:3822–3828.

Samulski, R. J., X. Zhu, X. Xiao, J. D. Brook, D. E. Housman, N. Epstein, and L. A. Hunter. 1991. Targeted interation of adeno-associated virus (AAV) into human chromosome 19. EMBO J. 10:3941–3950.

Shi, Y., E. Seto, L.-S. Chang and T. Shenk. 1991. Transcriptional repression by YY1, a human GLI-Kruppel-related protein, and relief of repression by adenovirus E1A protein. Cell 76:377–388.

Stillman, B. W., F. Tamanoi, and M. B. Mathews. 1982. Purification of an adenovirus-coded DNA polymerase that is required for initiation of DNA replication. Cell 31: 613–623.

Thrasher, A. J., M. de Alwis, C. M. Casimir, C. Kinnow, K. Page, J. Lebkowski, A. W. Segal, and R. J. Levinsky. 1995. Generation of recombinant adeno-associated virus (rAAV) from an adenoviral vector and functional reconstitution of the NADPH-oxidase. Gene Therapy 2:481–485.

Tratschin, J. D., J. Tal and B. J. Carter. 1986. Negative and positive regulation in trans of gene expression from adeno-associated virus vectors in mammalian cells by a viral rep gene product. Mol. Cell. Biol. 6:2884–2894.

Trempe, J. P. and B. J. Carter. 1988. Regulation of adeno-associated virus gene expression in 293 cells: Control of mRNA abundance and translation. J. Virol. 62:68–74.

Vincent, K. A., G. K. Moore, and N. L. Haigwood. 1990. Replication and packaging of HIV envelope genes in a novel adeno-associated virus vector system, p.353–359. In F. Brown, R. M. Chanock, H. S. Ginsberg, and R. A. Lemer, (eds.), Vaccines 90: Modem approaches to new vaccines including prevention of AIDS. Cold Spring Harbor Laboratory Press, Cold Spring Harbor, N.Y.

West, M. H. P., J. P. Trempe, J.-D. Tratschin and B. J. Carter. 1987. Gene expression in adeno-associated virus vectors: The effects of chimeric mRNA structure, helper virus, and adenovirus VA1 RNA. Virology 160:38–47.

Yang, Q., F. Chen and J. P. Trempe. 1994. Characterization of cell lines that inducibly express the adeno-associated virus Rep proteins. J. Virol. 68:4847–4856.

What is claimed is:

1. A composition useful for producing recombinant adeno-associated virus (AAV) with reduced levels of wild-type helper adenovirus, said composition comprising cells which have been transiently transfected with:
   (a) an AAV helper plasmid comprising nucleic acid sequences encoding AAV rep and cap proteins, or other source of AAV rep and cap proteins;
   (b) an adenoviral helper plasmid consisting essentially of adenovirus helper genes selected from the group consisting of E1A, E1B, E2A, E4, E4ORF6, E4ORF6/7, VA RNA and combinations of the foregoing; and
   (c) an AAV vector comprising first and second AAV ITRs or portions thereof, wherein said first and second AAV ITRs flank a DNA sequence encoding a polypeptide of interest, said DNA sequence being operably linked to a promoter DNA sequence;
wherein said composition contains reduced levels of adenovirus particles compared to co-infection of cells with AAV vector and wild-type helper adenovirus.

2. The composition of claim 1, wherein the AAV helper plasmid comprises an AAV rep gene, and said AAV rep gene is under the control of a heterologous promoter.

3. The composition of claim 1, wherein the adenoviral helper plasmid comprises AAV ITR sequences flanking the adenovirus helper genes, and said AAV ITR sequences allow the plasmid to replicate.

4. The composition of claim 2, wherein the AAV helper plasmid comprises an AAV cap gene, and said AAV cap gene is under the control of a heterologous promoter.

5. The composition of claim 4, wherein the AAV cap gene is under the control of a constitutively expressed heterologous promoter.

6. The composition of claim 4, wherein the AAV cap gene is under the control of the cytomegalovirus immediate early (CMV IE) promoter.

7. A method for producing recombinant adeno-associated virus (AAV) with reduced levels of wild-type helper adenovirus compared to co-infection of cells with AAV vector and wild-type helper adenovirus, said method comprising the steps of:
   (1) culturing a composition comprising cells which have been transiently transfected with:
      (a) an AAV helper plasmid comprising AAV rep and cap nucleic acid sequences encoding AAV rep and cap proteins;
      (b) an adenoviral helper plasmid comprising essential adenovirus helper genes selected from the group consisting of E1A, E1B, E2A, E4, E4ORF6, E4ORF6/7, VA and combinations of the above; and
      (c) an AAV vector comprising first and second AAV ITRs or portions thereof, wherein said first and second AAV ITRs flank a DNA sequence encoding a polypeptide of interest, said DNA sequence being operably linked to a promoter DNA sequence;
   in the absence of adenovirus particles and under conditions suitable for the production of recombinant AAV; and
   (2) purifying recombinant AAV produced therefrom.

8. The method of claim 7, wherein the AAV helper plasmid comprises an AAV rep gene, and said AAV rep gene is under the control of a heterologous promoter.

9. The method of claim 7, wherein the adenoviral helper plasmid comprises AAV ITR sequences flanking the adenovirus helper genes, and said AAV ITR sequences allow the plasmid to replicate.

10. The method of claim 8, wherein the AAV helper plasmid comprises an AAV cap gene, and said AAV cap gene is under the control of a heterologous promoter.

11. The method of claim 10, wherein the AAV cap gene is under the control of a constitutively expressed heterologous promoter.

12. The method of claim 10, wherein the AAV cap gene is under the control of the cytomegalovirus immediate early (CMV IE) promoter.

13. A method for producing recombinant adeno-associated virus (AAV) with reduced levels of wild-type helper adenovirus to co-infection of cells with AAV and wild-type helper adenovirus, said method comprising the steps of:
   (1) culturing a composition comprising cells which have been transiently transfected with:
      (a) an AAV helper plasmid comprising AAV rep and cap nucleic acid sequences encoding AAV rep and cap proteins;
      (b) an adenoviral helper plasmid consisting essentially of adenovirus helper genes E2A, E4 ORF6 and VA RNA, wherein the adenoviral helper plasmid comprises AAV ITR sequences flanking the adenovirus helper genes, and said AAV ITR sequences allow the plasmid to replicate; and
      (c) an AAV vector comprising first and second AAV ITRs or portions thereof, wherein said first and second AAV ITRs flank a DNA sequence encoding a polypeptide of interest, said DNA sequence being operably linked to a promoter DNA sequence;
   in the absence or reduced presence of adenovirus particles and under conditions suitable for the production of recombinant AAV; and
   (2) purifying recombinant AAV produced therefrom.

14. A method for producing recombinant adeno-associated virus (AAV) with reduced levels of wild-type helper adenovirus compared to co-infection of cells with AAV and wild-type helper adenovirus, said method comprising the steps of:
   (1) culturing a composition comprising cells which have been transiently transfected with:
      (a) an AAV helper plasmid comprising AAV rep and cap nucleic acid sequences encoding AAV rep and cap proteins;
      (b) an adenoviral helper plasmid consisting essentially of adenovirus helper genes E2A, E4 ORF6 and VA RNA, wherein the adenoviral helper plasmid comprises AAV ITR sequences flanking the adenovirus helper genes, and said AAV ITR sequences allow the plasmid to replicate; and
      (c) an AAV vector comprising first and second AAV ITRs or portions thereof, wherein said first and second AAV ITRs flank a DNA sequence encoding a polypeptide of interest, said DNA sequence being operably linked to a promoter DNA sequence;
   in the absence or reduced presence of adenovirus particles and under conditions suitable for the production of recombinant AAV; and
   (2) purifying recombinant AAV produced therefrom.

15. The hybrid helper plasmid of claim 14, wherein the AAV genes are selected from the group consisting of rep, cap and both rep and cap.

16. The hybrid helper plasmid of claim 14, wherein the adenoviral accessory genes are selected from the group consisting of E2A, E4ORF6, E4ORF6/7, VA RNA, and combinations of the foregoing.

17. The hybrid helper plasmid of claim 14, wherein said hybrid helper plasmid comprises AAV sequences flanking the AAV rep and cap genes, and the adenoviral accessory genes E2A, E4ORF6 and VA RNA.

* * * * *